(12) United States Patent
Taylor, Jr.

(10) Patent No.: US 6,218,945 B1
(45) Date of Patent: Apr. 17, 2001

(54) AUGMENTED MONITORING SYSTEM

(76) Inventor: John E Taylor, Jr., 19080 SW. 44th St., Dunnellon, FL (US) 34432

( * ) Notice: Subject to any disclaimer, the term of this patent is extended or adjusted under 35 U.S.C. 154(b) by 0 days.

(21) Appl. No.: 09/385,481

(22) Filed: Aug. 30, 1999

Related U.S. Application Data

(63) Continuation-in-part of application No. 09/229,023, filed on Jan. 12, 1999, now Pat. No. 6,160,481, which is a continuation-in-part of application No. 08/926,746, filed on Sep. 10, 1997, now Pat. No. 5,867,103.

(51) Int. Cl.$^7$ ................................................. G08B 21/00
(52) U.S. Cl. ................... 340/573.1; 340/539; 340/573.4; 340/825.49; 379/38
(58) Field of Search ............................ 340/573.1, 573.4, 340/539, 825.49; 379/38

(56) References Cited

U.S. PATENT DOCUMENTS

| | | | |
|---|---|---|---|
| 5,461,390 | * | 10/1995 | Hoshen ............................... 340/573.4 |
| 5,652,570 | * | 7/1997 | Lepkofker ........................... 340/573.1 |
| 5,731,757 | * | 3/1998 | Layson, Jr. ......................... 340/573.4 |
| 5,990,793 | * | 11/1999 | Bieback .............................. 340/573.1 |
| 6,054,928 | * | 4/2000 | Lemelson et al. ................. 340/573.4 |
| 6,100,806 | * | 8/2000 | Gaukel ............................... 340/573.4 |

* cited by examiner

*Primary Examiner*—Daniel J. Wu

(57) ABSTRACT

Cooperation between a monitored person device and a companion device allow for a relatively accurate determination of a locational reference for the monitored person device and therefore, a monitored person. This is accomplished while minimizing the weight of the monitored person device which is constantly transported by the monitored person during movement of the monitored person. The companion device may be either a fixed position type or, more preferred, a transportable type which may be moved about by the monitored person. These components of the companion device include those required to receive a signal, or signals, sufficient to allow for a determining of a locational reference of the companion device and those required to transmit a signal for eventual transfer to a central location. The monitored person device must have components which provide for transmitting a signal to the companion device, if within a communication range. Components of the system provide for a determination of a spacing and an orientation of the monitored person device relative to the companion device. When this information is combined with the information sufficient to allow for a determination of the locational reference of the companion device, the locational reference of the monitored person device may fairly accurately be made. The overall system of monitoring roaming persons may involve behavioral monitoring, medical monitoring or security monitoring.

20 Claims, 11 Drawing Sheets

*FIG. 9a*   *FIG. 9b*   *FIG. 9c*
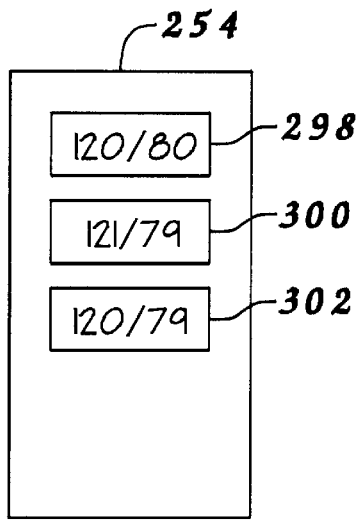
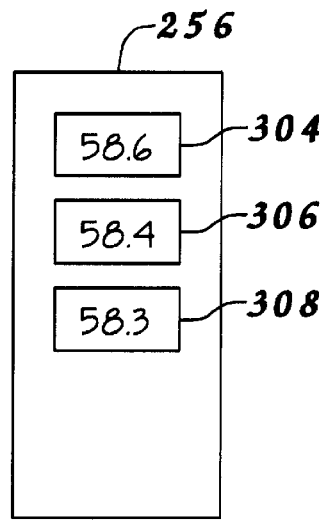
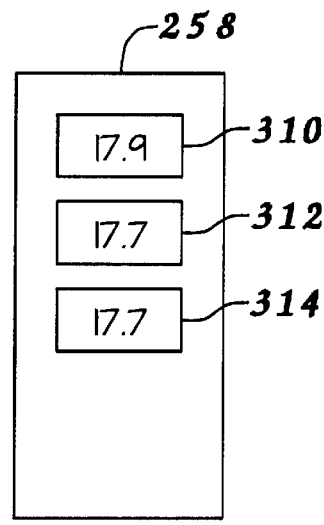
*FIG. 9d*   *FIG. 9e*   *FIG. 9f*
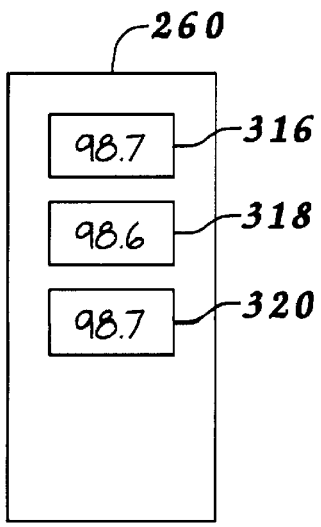
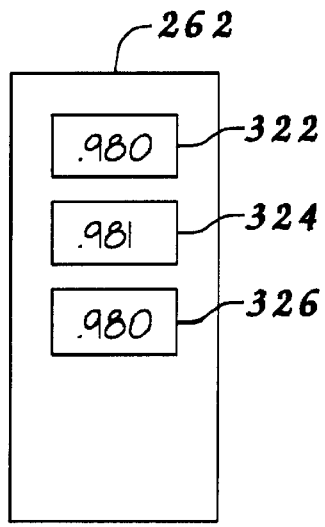
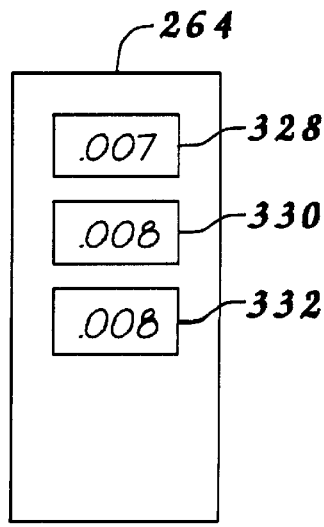

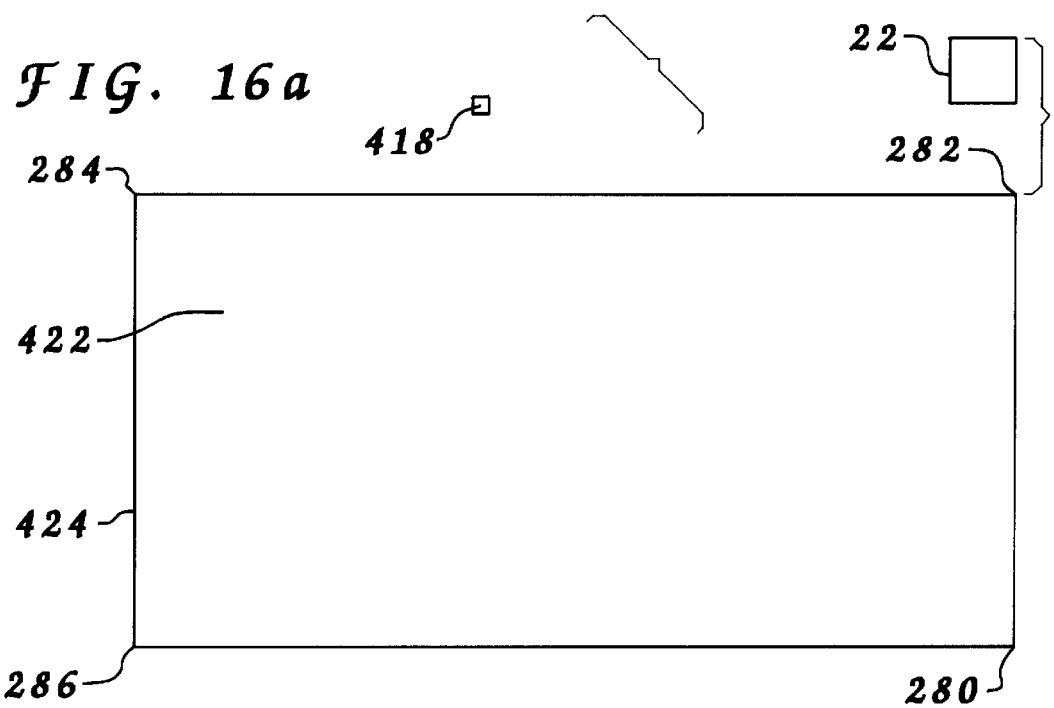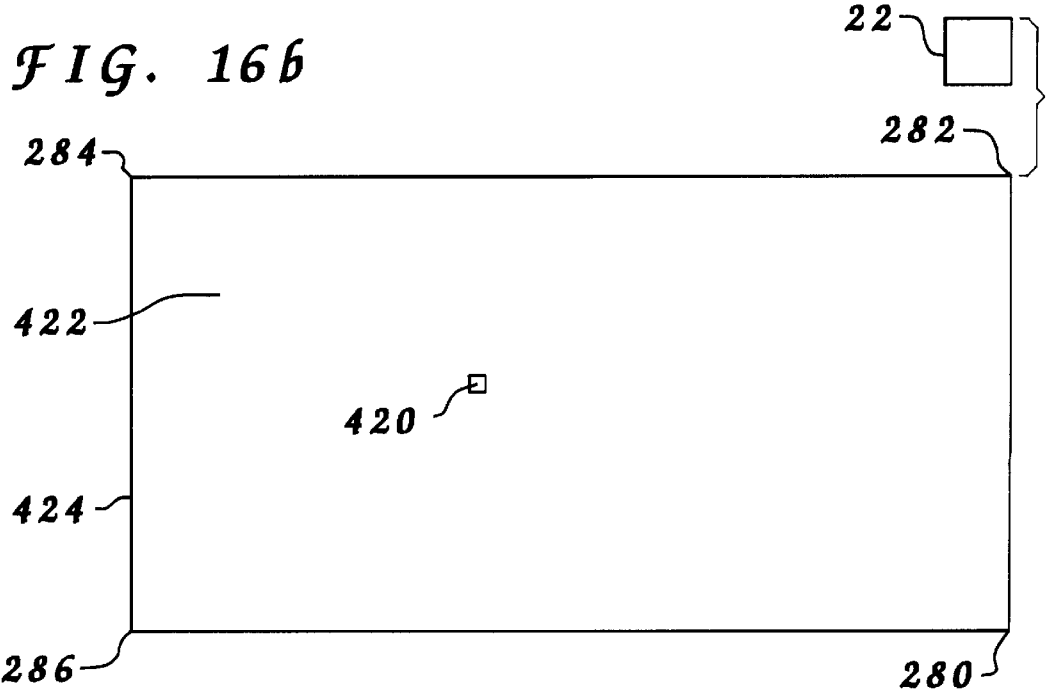

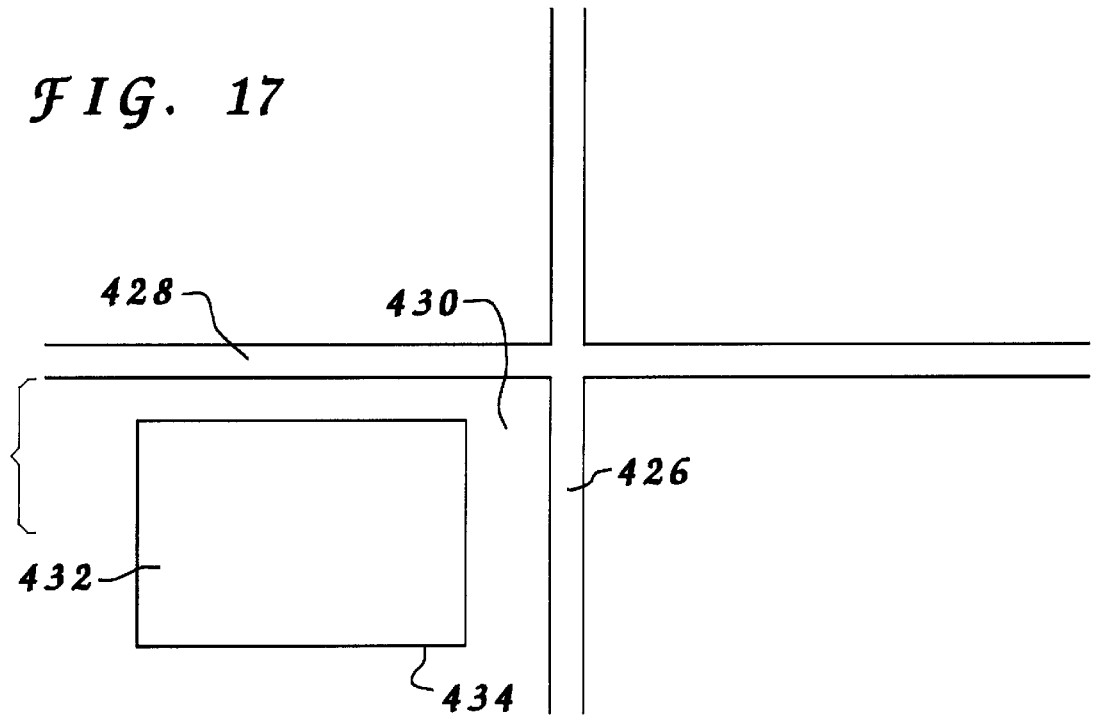

AUGMENTED MONITORING SYSTEM

CROSS-REFERENCE

This application is a continuation-in-part of Ser. No.: 09/229,023 filed Jan. 12, 1999, U.S. Pat. No. 6,160,481 entitled "Monitoring System", currently pending, which is a continuation-in-part of U.S. Pat. No. 5,867,103, Ser. No.: 08/926,746 filed Sep. 10, 1997, entitled "Monitored Person Tracking System". These applications are incorporated herein by this reference.

BACKGROUND

1. Field of the Invention

Generally, the invention relates to positional monitoring of persons. More specifically, the invention relates to such positional monitoring wherein at least one monitored person uses a combination of a monitored person device and a companion device, of either a fixed position type or a transportable type, wherein the combination cooperates to provide for a relatively accurate positional determination of the monitored person.

2. Description of the Prior Art

It has long been a desire to monitor where a person is at any given time. Numerous reasons exist for such monitoring including for emergency response, behavioral tracking and general personal security.

Referring now to emergency response, numerous medical conditions may exist which require immediate attention. Examples of such medical conditions may be broadly defined as occurring when there is a sudden deviation from acceptable limits. The underlying medical condition may have been known or unknown to the individual. Such a deviation from acceptable limits may require that the individual temporally modify his or her activity, may require introduction of a medicine or may require medical attention by trained medical personnel.

Currently when medical attention by trained medical personnel is suddenly required as a result of a crisis it usually falls to the individual or other individuals which observe the crisis to summon assistance. This is often not possible for the individual to do because of the specific medical crisis and the effect upon the individual. The individual may be alone at the time of the medical crisis. As is often the case, other individuals which observe the crisis may not be capable of readily identifying the problem. In any event, such a request for medical assistance is often less efficient than desired due to misdirection to the location of the individual having the medical crisis. This may result in a loss of valuable time from the onset of the medical crisis to arrival of the trained medical personnel.

Referring now to behavioral tracking, our society has been compelled to confine individuals as a result of their behavior which has been deemed unacceptable to the best interest of society. Historically, such confinement has occurred at centralized locations where numerous confinements occur simultaneously. It is expensive for society to maintain such centralized locations due primarily to construction cost, upkeep cost, supervisory personnel expense and medical care for the persons being confined. These persons being confined represent both those convicted of committing a crime as well as those accused of committing a crime, but awaiting trial.

Our society has begun to seek alternative means of confining those individuals convicted of committing a crime or accused of committing a crime while awaiting trial where those individuals are deemed to pose an acceptable risk to society. Parole, probation and house arrest programs have existed for some time and are being extensively utilized by the justice system for certain type of crimes.

Additionally, our society has recently made progress toward restricting the activities of certain habitual offenders of certain type of crimes even following completion of court appointed sentences. These restrictions are coming in the form of civil actions as compared to criminal actions. Some circumstances require continued conventional confinement while others require site confinement or other monitoring of activities. Examples of such crimes include child molestation and other sex crimes.

Referring now specifically to site confinement, a common type of behavioral monitoring, it is conventionally known to provide for such site confinement of individuals wherein means are provided within the respective system to indicate that a respective individual has violated boundaries of their respective site. Several of these systems include means to detect tampering with various elements of the system.

The most common type of such a site confinement system comprises three devices. These devices are a central processing unit, at least one transportable device and at least one base unit. The transportable device, which securely attaches to the individual being confined, comprises communication means to communicate with the base unit. The base unit, which is positioned within the boundaries of the confinement site, comprises two types of communication means. The first of the communication means allows the base unit to at least receive a signal from the transportable device. Generally, this communication is a wireless broadcast. The second of the communication means allows the base unit to at least send a signal to the central processing unit. Generally, this communication is over a ground based telephone system. When communication is not present from the transportable device to the base unit, the base unit, utilizing the second communication means, communicates with the central processing unit to notify an oversight authority of a possible violation of the confinement by the individual. As can readily be seen such systems have a general deficiency in that they are bound to a single designated site location. Several systems have been proposed which allow for a wider tracking of individuals.

It is a desire, for various useful reasons, to provide a method for monitoring at least a locational position of a person beyond that available utilizing a site confinement system. Various methods, and associated systems, exist to provide for such roaming monitoring. Generally, such roaming monitoring systems can be defined as belonging in one of two groups. Such roaming monitoring methods all share certain requirements without regard for the specific reason for such monitoring. A first requirement is that means must be provided to determine a locational position of at least one of the moveable components. This requirement necessitates structural components which must be moved about with the monitored person. A second requirement is that means must be provided to transmit, at some point of time, information about such locational position to other components employed within the method. Various other requirements will exist depending upon the design and purpose of any select system.

Systems of the first group provide for a combination of a transportable device and a body worn device. Such systems provide for a capacity to fairly accurately determine a position of the transportable device. The components required to fulfill the locational determination requirements of this group are housed within the transportable device. The monitored person moves the transportable device around during movement of the monitored person to retain the transportable device within a definable communication range with the body worn device. Systems within this group only provide for locational tracking of the transportable device while indicating the position of the monitored person based upon confirmation that the respective transportable device for the respective monitored person is within a free range zone about the respective body worn device. Systems based upon this group enjoy the benefit of housing bulky components within the transportable device which must be manipulated only when the monitored person desires to move to a location beyond the then existing free range zone. This provides the benefit of a significantly reduced weight, both in terms of required components and a power supply therefor, which must be constantly transported by the monitored person. Unfortunately, in order to be practical in application, the free range zone, generally a radius but subject to other communication factors, about the body worn device must be relatively large to prevent loss of communication between the body worn device and the transportable device as the monitored person moves about during routine activities. For those systems utilizing emergency response, this may require an excessive period of search time to locate the monitored person, or even prevent location of the monitored person. For those systems utilizing behavioral tracking, this may provide for the monitored person to be within an excluded site while the system reports that the transportable device remains outside of the perimeter of the excluded site. As can readily be seen, systems based upon this group have various failures which prevent acceptance of such systems within the industry.

Systems of the second group provide for a body worn device to be the only component in the possession of the monitored person. Such systems provide for a capacity to fairly accurately determine a position of the monitored person. Unfortunately, such systems require that all the required components be transported with the monitored person constantly and that an adequate power supply exist to support operation of those components. This results in a relatively heavy and bulky body worn device.

As can be seen various attempts have been made to provide for a method of monitoring the location of roaming monitored persons. These attempts have been less efficient than desired. As such, it may be appreciated that there continues to be a need for a system which may accurately determine the location of the roaming monitored person while providing for a fairly small and light device which must be constantly in the possession of the monitored person. The present invention substantially fulfills these needs.

SUMMARY

In view of the foregoing disadvantages inherent in the known types of monitoring systems, your applicant has devised a system which provides for identifying a locational reference indicative of a locational position of a monitored person. The system has a monitored person device, a companion device, of either a fixed position type or a transportable type, computational means and conversion means. When the companion device is of a transportable type it will be manually moved about by the monitored person so that the monitored person retains the companion device within a predefined spacing about the monitored person. The companion device has first receiving means, second receiving means and transmitting means. The first receiving means provides for receiving a signal from a detached sending unit. The transmitting means provides for sending a signal to a detached receiving unit. The monitored person device is moved about with the monitored person during movement of the monitored person. The monitored person device has transmitting means to provide for generating a signal for reception by the second receiving means of the companion device. The computational means provides for determining a locational position of the monitored person device utilizing at least the signal from the detached sending unit received by the first receiving means of the companion device and the signal from the monitored person device received by the second receiving means of the companion device. A locational position of the companion device is determinable then a locational position of the monitored person device is determined based upon a determining of a spacing and an orientation of the monitored person device relative to the companion device. The conversion means provides for converting the locational position of the monitored person device to the locational reference for the monitored person.

My invention resides not in any one of these features per se, but rather in the particular combinations of them herein disclosed and it is distinguished from the prior art in these particular combinations of these structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore a primary object of the present invention to provide for a system wherein a cooperation exists between a monitored person device and a companion device to provide for a relatively accurate determination of a locational position of the monitored person device following a relatively accurate determination of a locational position of the companion device wherein the determination of the locational position of the monitored person device is based upon a spacing and orientation of the monitored person device from the companion device.

Other objects include;

a) to provide for determining a locational reference of a locational position of the monitored person device based in part upon at least one signal received by the companion device wherein the signal is generated by at least one detached sending unit and wherein the signal, at least in part, allows for a determination of a locational reference for the companion device.

b) to provide for monitoring of a bodily signal produced by the monitored person.

c) to provide for a notification to a central location of any indication of a possible medical emergency of the monitored person when physiological readings are outside of a range from a baseline reading for the respective monitored person.

d) to provide for a medical monitoring of individuals wherein a notification may take place automatically by notifying the proper emergency personnel of the individuals condition and location in the advent that a monitored physiological sign moves outside of a desired range for the individual.

e) to provide for an active response through a digital readout directly to the monitored person to provide instructions or commands to the monitored person in response to a variation in a bodily signal measurement of the monitored person beyond a predetermined range.

f) to provide for an active response through an audio output directly to the monitored person to provide instructions or commands to the monitored person in response to a variation in a bodily signal measurement of the monitored person beyond a predetermined range.

g) to provide for a bi-directional communication between the monitored person and oversight personnel in response to a variation in a bodily signal measurement of the monitored person beyond a predetermined range.

h) to provide for a monitored person device which may be secured to a monitored person.

i) to provide for detecting tampering with the monitored person device.

j) to provide for generating an associated occurrence reference indicative of a time span related to a locational reference and/or a bodily signal reference.

k) to provide for a storage of at least a series of locational references and/or bodily signal references along with associated occurrence references within a database.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated the preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein;

FIG. 9a through FIG. 9f are plan views of representations of various databases.

FIG. 16a and FIG. 16b are plan views of an excluded site and two (2) locational references in alternative orientations thereto.

FIG. 17 is a plan view of an intersection of two (2) streets and a comparative location reference.

DESCRIPTION OF THE PREFERRED EMBODIMENTS

Figure 1:
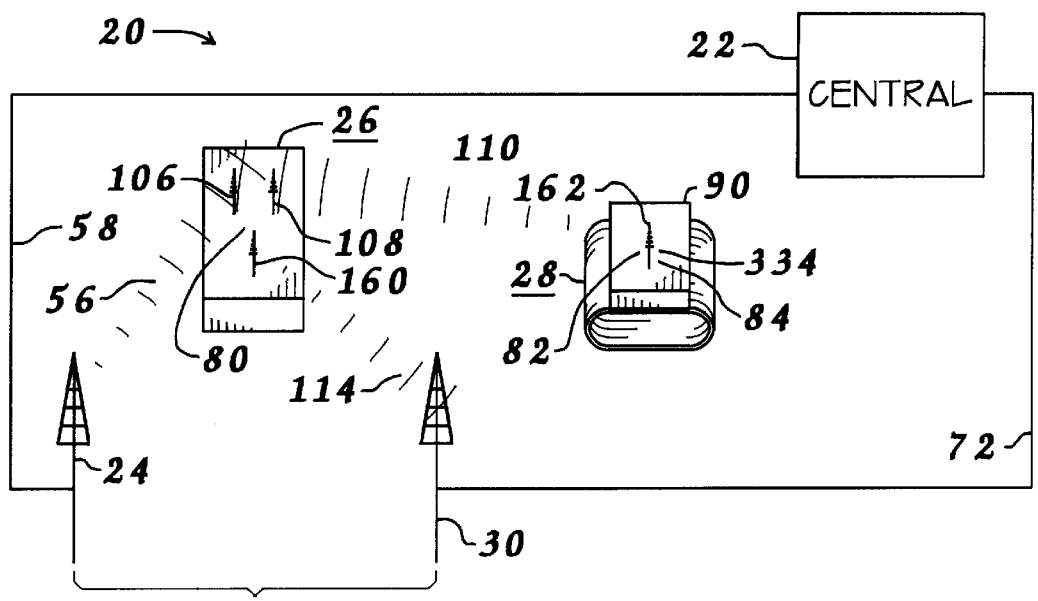
FIG. 1 is an illustration of an embodiment of a system having features of the present invention.

Reference is hereafter made to the drawings where like reference numerals refer to like parts throughout the various views.

Overview

Many different systems having features of the present invention are possible. The following description describes the preferred embodiment of select features of those systems and various combinations thereof. These features may be deployed in various combinations to arrive at various desired working configurations of systems. The system may be used for many useful purposes. These purposes include behavioral monitoring, medical monitoring or overall security monitoring.

The term transmitting means as used herein defines any of the conventional wireless broadcast methods known in the art and is not limited to an antenna or any specific type of antenna. The term receiving means as used herein defines any of the conventional wireless reception methods known in the art and is not limited to an antenna or any specific type of antenna.

Figure 3:
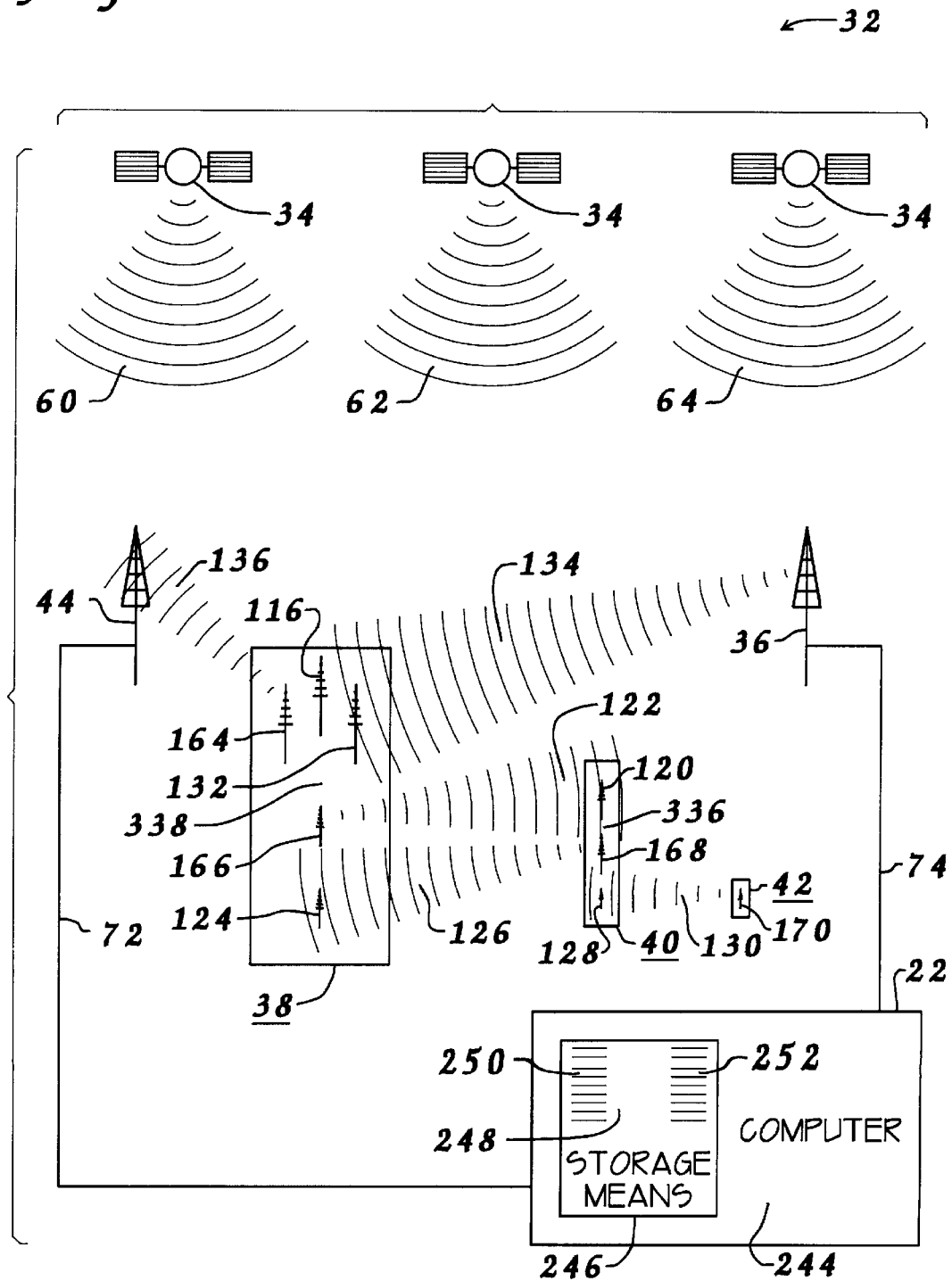
FIG. 3 is an illustration of another embodiment of a system having features of the present invention.
Figure 4:
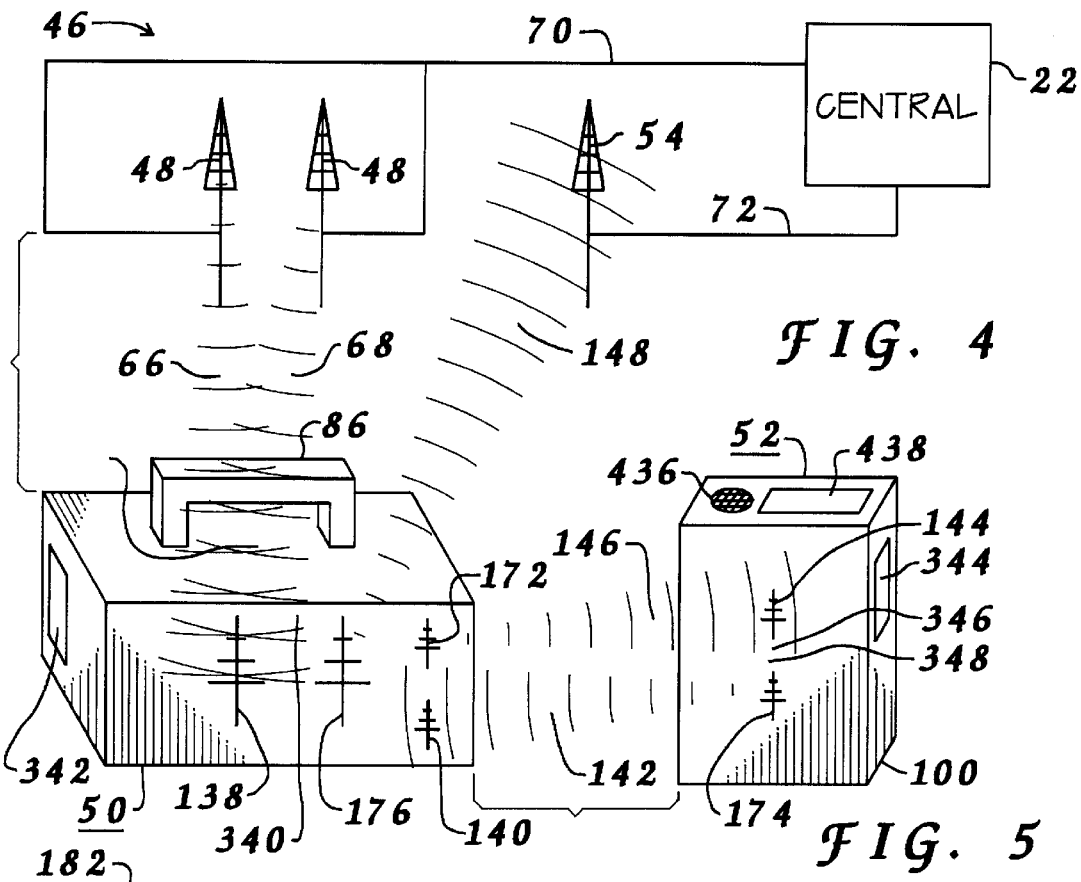
FIG. 4 is an illustration of another embodiment of a system having features of the present invention.

FIG. 1 depicts a system 20 having features of the present invention. System 20 has a central location 22, a detached sending unit 24, a transportable device 26, a monitored person device 28 and a receiving unit 30. Transportable device 26 is a companion device to monitored person device 28. FIG. 3 depicts a system 32 having features of the present invention. System 32 has central location 22, a plurality of detached sending units 34, a transmitting unit 36, a companion device 38, a monitored person device 40, a medical monitoring device 42 and a receiving unit 44. Many of the features depicted for companion device 38 may be eliminated when companion device 38 is not intended to be repositioned in the future. FIG. 4 depicts a system 46 having features of the present invention. System 46 has central location 22, detached sending units 48, a transportable device 50, a monitored person device 52 and a receiving unit 54. Transportable device 50 is a companion device to monitored person device 52. Many variations of such systems are possible without departing from the spirit of the present invention.

Central Location

It is a requirement of the present invention that a central location, or locations, be provided which will receive communication from and/or send communication to at least select deployed components of any deployed system. This communication will be specific to the overall configuration of the deployed system. Generally, the central location will; receive communication from deployed components and/or send communication to deployed components and/or store information and/or perform computational calculations on information and/or allow access to information by supervisory personnel. While the central location may be dedicated to a monitoring of a system of the present invention, it is possible that the central location may be non-dedicated, or have a primary and/or secondary purpose other than monitoring the system of the present invention. Examples of such non-dedicated central locations include public and private institutions such as police stations, fire department stations, existing burglar alarm monitoring locations, hospitals, retirement homes, nursing homes or schools. Therefore, the term central location as used herein refers broadly to a location or locations which house the various fixed position equipment of the present invention.

FIG. 1, FIG. 3 and FIG. 4 depict central location 22 which houses various equipment of the respective system. Such a central location would exist without regard for the specific configuration of the respective system deployed. Supervisory personnel, not shown, would have access to exert control over, or otherwise interface with, the overall system at central location 22.

Detached Sending Units

It is a requirement that a method exist to provide for making a determination of a locational position of the respective companion devices, and eventually the respective monitored person devices, in the possession of the respective monitored person. To this end, a signal, or signals, must be produced by at least one detached sending unit. This signal, or signals, is subsequently received by at least one other component of the system wherein an evaluation is made to provide for a determination of the location of a respective companion device. The detached sending units may be fixed ground based, moveable ground based, orbital or a combination thereof. When the companion device is a fixed position device, the companion device may have components to enable a determination to be made of a locational position following a computational operation on the signal(s) received from the detached sending unit(s). Alternatively when the companion device is a fixed position device, the signal received from the detached sending unit may directly or indirectly contain a locational reference of the locational position of the companion device as exampled by a direct entry of coordinates inputted during an installation procedure.

FIG. 1 depicts a single detached sending unit 24, in this embodiment being a ground based transmission tower, and capable of broadcasting a signal 56. Signal 56 is received by transportable device 26. Signal 56 may be independently created or signal 56 may be transferred from central location 22 utilizing a coupling 58.

FIG. 3 depicts a plurality of detached sending units 34, in this embodiment being orbital based transmission satellites, and each capable of broadcasting a unique signal 60, 62 and 64 respectively. Utilization of such orbital satellites in positional systems is well known in the art and may readily be employed within the present invention. Signals 60, 62 and 64 are received by companion device 38. Signals 60, 62 and 64 most likely will be independently created without input from other components of system 32.

FIG. 4 depicts the use of a plurality of detached sending units 48 similar to that utilized in system 20, shown in FIG. 1. Each detached sending unit 48 is capable of broadcasting a signal 66 and a signal 68 respectively. Signals 66 and 68 are received by transportable device 50.

Relay Equipment

It is a requirement that the central location(s) be capable of communicating, at least in one direction, with respective companion devices. This communication may be either from the central location to respective companion devices, from respective companion devices to the central location or both. For companion devices of the transportable type, preferably such communication at least in part involves wireless communication utilizing either a ground based system or an orbital system or both. Many such wireless systems are conventionally known in the art and many of these systems may be utilized for the present invention. Additionally, for the sake of economics and without regard for whether the companion device is fixed or transportable, it is desirable to have such communication transfers utilize, at least partially, existing ground based communication systems, as exampled by phone lines.

Figure 6:
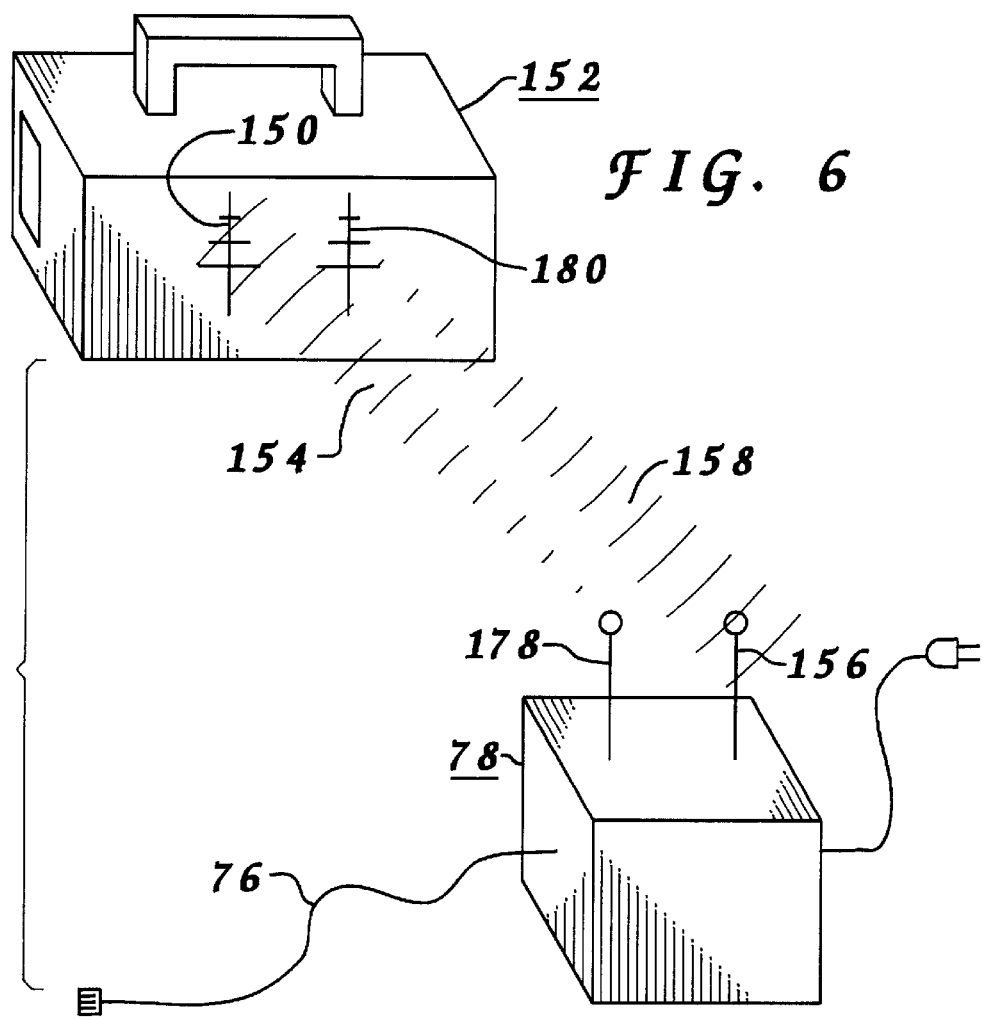
FIG. 6 is a perspective view of another embodiment of portions of a system having features of the present invention.

FIG. 1 depicts coupling 58 which provides for communication from central location 22 to detached sending unit(s) 24. FIG. 4 depicts a coupling 70 which provides for communication from central location 22 to detached sending units 48. FIG. 1, FIG. 3 and FIG. 4 depict a coupling 72 provides for communication from receiving units 30, 44 and 54 to central location 22 respectively. FIG. 3 depicts a coupling 74 which provides for communication from central location 22 to transmitting unit 36. FIG. 6 depicts a phone line 76 which allows a base station 78 to communicate with the central location, not shown in this view.

Combination of Monitored Person Device and Companion Device

It is a requirement of the present invention that a combination of two (2) devices be deployed with each monitored person. The devices of this combination would be a monitored person device and a companion device. The companion device would be either of a fixed position type or of a transportable type.

When the fixed position type companion device is utilized a fixed position device is provided which is fixedly positioned and about which the monitored person device, and therefore the monitored person, could freely move. Such a system would allow for an initial determination of the location of the fixed position device to be made. Such a determination may be made utilizing components contained within the fixed position device or, more likely, would have a separate device make such a determination at the time of placement of the fixed position device with entry of such information into the system. Then, using the principles of the present invention, a determination may be made of the spacing and the orientation of the monitored person device relative to the fixed position device to provide the desired determination of the locational position of the monitored person device. Such a system may be utilized to monitor persons in several situations including institutional settings such as retirement homes.

It is possible to provide for other devices to interact with components of systems having features of the present invention. One example of such an interaction may involve an institutional type setting and an interaction involving a receiver unit attached to automated doors of the institution. The receiver unit of the doors may selectively restrict egress of select monitored persons and may include notification of such attempted egress to supervisory personnel. In certain settings, as exampled by retirement homes, certain persons may not be allowed to leave the facility unsupervised at any time. Other person may be allowed to leave based upon individual schedules of certain hours of certain days. Such an interaction of a system having features of the present invention may prevent individuals from being placed in dangerous situations outside of the facility while providing for rapid locating of those which inadvertently leave the facility unsupervised.

Each monitored person will have a monitored person device which is unique for the respective monitored person. Typically, each monitored person will also have a unique companion device for the respective monitored person. When the companion device is of a transportable type this unique deployment will be a requirement. In certain configurations each monitored person will have a unique companion device when the companion device is of the fixed position type. Alternatively, a respective companion device of the fixed position type may service several, or even many, monitored person devices.

Typically the combination of two (2) components will involve a unique pairing of a companion device and a monitored person for each monitored person. In such a combination certain functions may be performed by the companion device thus eliminating the requirement of providing structures on or in the monitored person device to perform those functions. This provides for a reduction in the required weight of the monitored person device, which must be carried by, or attached to, the monitored person, without loss of the otherwise desired function. One example of such a combination provides for structures to provide for short range communication at least from the monitored person device to the companion device while providing bulkier structures on the companion device to provide for transmission of a signal for eventual transfer to the central location.

It is possible to provide the companion device, when of the transportable type, with a sensor, or sensors, to determine if the companion device has been moved. Such an arrangement would provide for a determination of a locational position of the companion device only while in motion and once subsequent to cessation of such motion. This provides for conservation of power which would be required to continually determine a locational position when such locational position has not changed since the last determination. Alternatively, it is possible to provide for a predetermined schedule of such determinations or a combination thereof.

It is possible to provide for components of the monitored person device to have locational determining means which selectively operate independent of the companion device. When the monitored person device is within communication range of the companion device these components having locational determining means are not powered and therefore do not operate. Thus, when within communication range with the companion device, a spacing and orientation in combination with the locational determining of the companion device provide for the locational determining of the monitored person device. In the instance that such communication is broken, these previously dormant components of the monitored person device are activated and a determination independent of the companion device is made of the locational position of the monitored person device. Such a system would require that the transmitting means of the monitored person device be capable, at least while operating in this independent state, of communicating with the overall system. Alternatively, such locational determining components of the monitored person device may be activated occasionally to provide for confirmation of the accuracy of the locational determining means normally used by the overall system.

It is possible, and in certain configurations desirable, to provide for the companion device, when of the transportable type, to appear to be some other structure as conventionally carried about by persons while performing their respective daily activities. While applicable to all systems utilizing features of the present invention, this feature is particularly desirable for behavior monitoring wherein a social stigma may be attached to such apparent monitoring. Examples of such structures which are routinely carried about by persons include cellular phones, pagers, notebook computers, other small electronic devices and briefcases amongst others. One example of this involves combining the functions of the monitored person device into an operational cellular phone. This is particularly desirable due to the fact that many persons routinely retain their cellular phone with them at all times while moving about while performing their daily activities.

Similarly, it is possible to conceal the companion device of the transportable type in a backpack, handbag or some other structure normally carried by persons vulnerable to abduction. When a person abducts someone, generally they will attempt to draw as little attention to their activities as possible. Therefore, occasionally they will take along a book bag or backpack of a child or the purse of a woman which they are abducting in order to provide as much time as possible before concern is raised about the location of the owner of abandoned property left behind. When this occurs it may allow for a tracking and speedy rescue of the abducted person by the proper authorities.

It is possible to provide for the companion device of the transportable type to receive signals from two (2) separate and distinct systems of detached sending unit(s). This provides for the system of the present invention to have information from which two (2) separate sets of calculations can be performed to determine two (2) separate locational references for the companion device of the transportable type. These two (2) locational references may be combined to provide for a more accurate locational reference than that available from either of the separate systems of detached sending unit(s) individually.

The companion device, of either type, will comprise at least means to receive a signal from a detached sending unit, means to transmit a signal for eventual reception by the central location, and means to receive a signal from the respective monitored person device. The monitored person device will comprise at least means to transmit a signal for reception by the respective companion device.

Various optional features may be included with either the companion device or the monitored person device. An anti-theft device, as conventionally known in the art, is one example of such an optional feature. Another example places a panic button on at least the monitored person device which may be selectively activated by the monitored person to summon assistance from the oversight authorities.

The companion device of the transportable type may have a base station which it is placed in direct contact with during certain time periods. While in such contact the power supply of the companion device of the transportable type may be recharged and communication with the central location may occur.

FIG. 1, used as an example but also see FIG. 3 and FIG. 4, depicts transportable device 26 and monitored person device 28. Transportable device 26 of FIG. 1 may be disguised as a notebook computer which may be moved about by the monitored person, not shown in this view, without concern for recognition of the device by observers as being part of a monitoring system. As more fully disclosed elsewhere herein, information may be produced to allow for a determination of a locational position 80 for transportable device 26. Additionally, information may be produced to allow for a determination of a relative position 82 (spacing and orientation) of monitored person device 28 relative to transportable device 26, assuming monitored person device 28 is within a communications range from transportable device 26. Utilizing these groups of information, it is possible to relatively accurately determine a locational position 84 of monitored person device 28.

Preferable, the companion device of the transportable type would be easy to carry by the monitored person. FIG. 4 depicts transportable device 50 having a handle 86 which makes such transport easy and convenient.

Securing Means

Certain systems having features of the present invention will provide for the monitored person to voluntarily transport the monitored person device therewith. In these instances it is not necessary to provide any securing means other than that desired to provide for convenient transport by the monitored person. This may involve many attachment means as conventionally known in the art, as exampled by a belt clip as conventionally utilized with pagers.

Certain systems having features of the present invention will provide for the monitored person to be compelled, or otherwise required, to retain the monitored person device in extremely close proximity to the person. This may be for several useful purposes as exampled by medical monitoring or tracking of a person under court, or other administrative, order. When medical monitoring is being performed, the specific type of monitoring will dictate to a certain extent the type of securing means utilized. When tracking of a person under court or administrative order is being performed, the means to secure may involve surrounding engagement of a portion of the body of the monitored person or may involve implantation. The preferred method of securement in these instances is the surrounding engagement method. The most obvious attachment locations for such attachment being around a wrist, around an arm, around an ankle, around a leg, around the chest, around the waist or around the neck. Implantation is possible, though less desirable.

Figure 2:
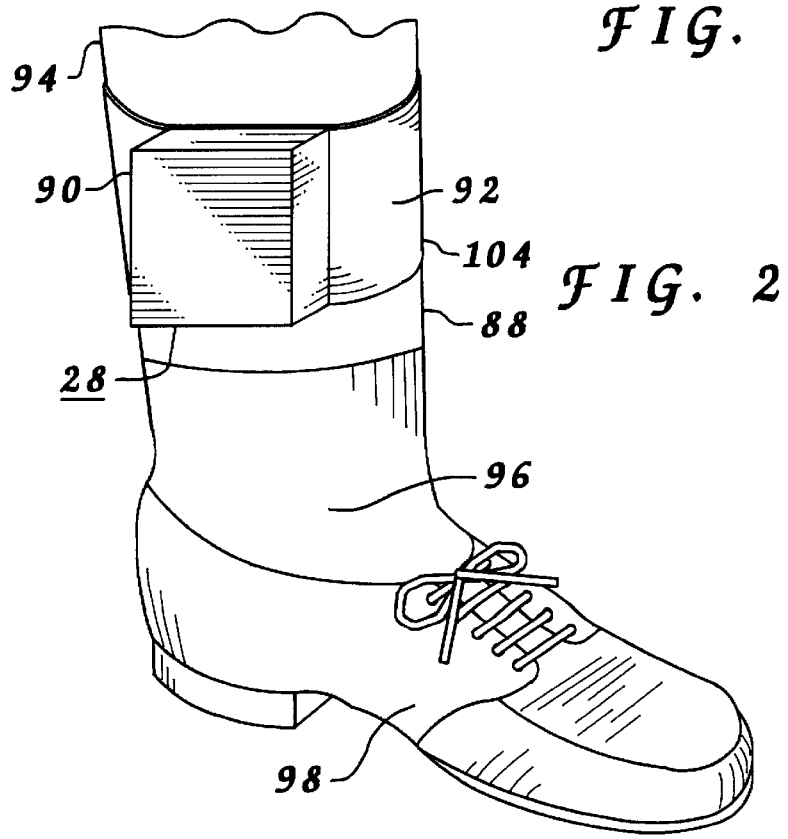
FIG. 2 is a perspective view of an embodiment of a monitored person device, as depicted in FIG. 1, attached to a monitored person.

FIG. 1 and FIG. 2 depict monitored person device 28 which may be secured to a monitored person 88, see FIG. 2. Such securing is preferred in certain configurations and is generally required when behavioral monitoring is occurring. Monitored person device 28 comprises a housing 90 and a band 92. Band 92 surrounds a leg 94, at an ankle 96, and locks to housing 90 to secure monitored person device 28 to monitored person 88, see FIG. 2. Band 92 is adjusted to be of a sufficient length that monitored person device 28 will not move past a foot 98, see FIG. 2.

Alternatively, the monitored person device may simply be carried by the monitored person. FIG. 4 depicts a housing 100 of monitored person device 52 in a convenient form as may be readily placed in a pocket or purse. A particularly expedient method of attachment involves a belt clip as known in the art for numerous objects as exampled by pagers.

Figure 8A:
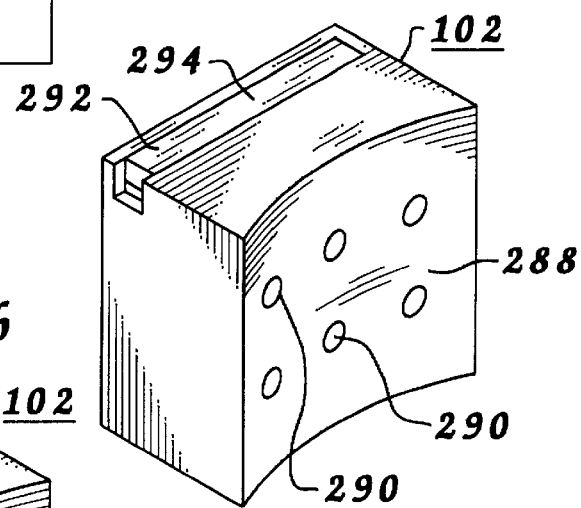
FIG. 8a and FIG. 8b are perspective views of a portion of an embodiment of a monitored person device in alternative operational positions.
Figure 8B:
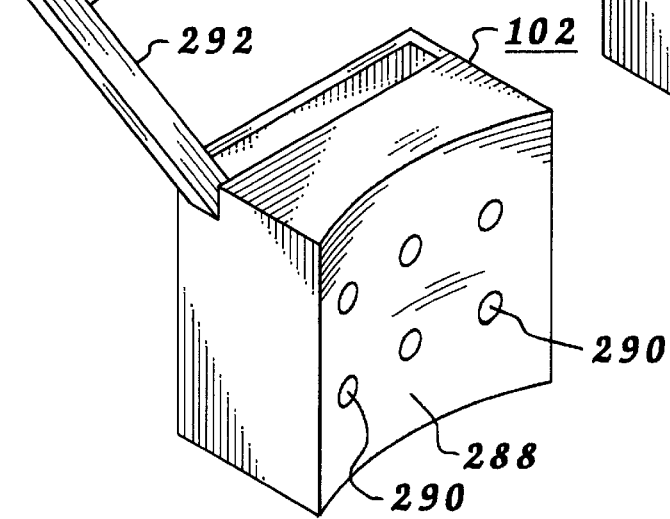

In certain system configurations it is a desire to have the monitored person device retained in contact with the skin of the monitored person. FIG. 8a and FIG. 8b depict a monitored person device 102, depicted without a band, as may be secured to a monitored person, not shown in these views.

Tamper Detection Means

Certain systems having features of the present invention will require that means to detect tampering be provided. Where the securing means involve surrounding engagement of a portion of the body of the monitored person, this will require that the surrounding band retain its prior integrity. This will involve means to ensure that the surrounding band is intact and, if connected to a housing, that such connections are intact. When tamper detection means are provided it is a strong desire that means be provided to detect any tampering with the housings of both the monitored person device and the companion device.

In certain configurations, and particularly when behavioral monitoring is occurring, it is a strong desire that the monitored person not be able to remove the monitored person device attached thereto. FIG. 2 depicts band 92 having a severing detection device 104 contained therein, as conventionally known in the art. Severing detection device 104, contained within, or about, band 92, connects, at opposing end thereof, to housing 90. As conventionally known in the art, equipment, not shown, contained in monitored person device 28 is capable of determining and reporting if any deviation in power through severing detection device 104 is detected. This prevents bypassing power transfer along severing detection device 104 while allowing for the severing of severing detection device 104. Similar equipment, conventionally known and not shown, allows for a detection of tampering with housing 90 or any other component of monitored person device 28.

Transmission Acquisition Means

It is a requirement that the central location eventually receive the signal(s) transmitted by each respective companion device. It is a requirement that each respective companion device receive the signal(s) transmitted by the detached sending unit(s). It is a requirement that each respective companion device receive the signal(s) transmitted by the respective monitored person device. Numerous types of receiving equipment, and relay equipment, as conventionally known in the art, may be employed to facilitate such respective transmission acquisition means.

In certain deployments it is a strong desire that the monitored person device further comprise transmission acquisition means to provide for receiving a signal sent by the companion device or other components of the system. The signal received may be data containing instructions from the companion device or transferred from the central location.

The signal transmitted by the companion device may be sent via direct contact with a base unit, indirect contact with a base unit or general wireless broadcast. Following transmission of the signal by the companion device it is a desire to acquire that signal at the central location. This acquisition may be directly by the central location or, more likely, will involve intermediate reception by other equipment which then transfers the signal on to the central location. (The term central location is not intended to be limited to one physical location for the tracking system, but rather a location, or locations, where data is gathered from distinct companion devices.)

Referring now to FIG. 1, a reception antenna 106 is depicted as contained within, or about, housing 90 of transportable device 26. Reception antenna 106 is capable of receiving signal 56, or signals, as sent by detached sending unit 24, in this example a ground based unit. A short range reception antenna 108 capable of receiving a signal 110 as sent by monitored person device 28. Receiving unit 30 is capable of receiving a signal 114 as sent by transportable device 26. Central location 22 is capable of receiving data contained within signal 114 following relay from receiving unit 30.

Referring now to FIG. 3, a reception antenna 116 is depicted as contained within, or about, a housing 118 of companion device 38. Reception antenna 116 is capable of receiving signals 60, 62 and 64 from detached sending units 34. A short range reception antenna 120 is contained within, or about, monitored person device 40 which is capable of receiving a signal 122 produced by companion device 38. A short range reception antenna 124 is contained within, or about, companion device 38 which is capable of receiving a signal 126 produced by monitored person device 40. A very short range reception antenna 128 is contained within, or about, monitored person device 40 which is capable of receiving a signal 130 produced by a medical monitoring device 42. Companion device 38 contains a reception antenna 132 capable of receiving a signal 134 from transmitting unit 36. Receiving unit 44 is capable of receiving a signal 136 from companion device 38.

Referring now to FIG. 4, a long range reception antenna 138 is depicted as contained within, or about, transportable device 50. Long range reception antenna 138 is capable of receiving signals 66 and 68 from detached sending units 48. A short range reception antenna 140 of transportable device 50 is capable of receiving a signal 142 from monitored person device 52. A short range reception antenna 144 of monitored person device 52 is capable of receiving a signal 146 from transportable device 50. Receiving unit 54 is capable of receiving a signal 148 from transportable device 50 for subsequent transfer to central location 22 utilizing coupling 72.

Referring now to FIG. 6, a short range reception antenna 150 of a transportable device 152 is depicted as being capable of receiving a signal 154 from base station 78. A short range reception antenna 156 of base station 78 is depicted as being capable of receiving a signal 158 from transportable device 152. Phone line 76 of base station 78 is capable of receiving a signal from and/or sending a signal to other components of the system, not shown in this view.

While separate elements are depicted on respective devices in the various views for reception of signals from different components of the various depicted systems, a single element may act to receive plural signals from separate components if desired. Similarly, where a single element is depicted to receive a signal, multiple elements may be employed.

Transmitting Means

In various configurations, it is a desire that at least two (2) select components moved about with the monitored person. These components are the companion device and the monitored person device. Each of these components must have transmitting means to provide for sending a signal to another component of the overall system. The signal sent may be data containing information about the monitored person or may be data giving further instruction to, or seeking further instructions from, other components of the system.

It is a requirement that the companion device be capable of sending a signal for eventual reception by the central location. It is also a requirement that the monitored person device be capable of sending a signal for reception by the companion device. Optionally, means may be provided for the companion device to send a signal for reception by the monitored person device. When required, components attached to the monitored person may communicate with other components to provide for sending bodily signal data about the monitored person.

The means to transmit a signal from the companion device to the central location may involve sending the signal following a direct contact with a base unit, utilizing an indirect wireless contact with a base unit or may utilize a wireless broadcast. The direct contact with a base unit is exampled by having a lead from the base unit which periodically is plugged into the companion device or having the companion device periodically placed in physical contact with the base unit wherein matching contacts make contact. The indirect wireless contact with a base unit is exampled by an infrared link as conventionally known for communication between detached electronic equipment, as exampled by such communication between a desktop computer and a laptop computer. The wireless broadcast is exampled by cellular or radio broadcast.

The companion device may immediately transfer a signal containing data following receipt of the data or immediately following creation of the data. Alternatively, the companion device may have means to allow for onboard storage of data for batch transfer at a later time. When batch transfer is employed, such transfer may be on a routine schedule via wireless transmission, or may be established on a less rigid schedule over ground based system, as exampled by phone lines.

The means to transmit a signal from the monitored person device to the companion device will most likely involve wireless transfer. Due to the requirement that the monitored person stay within a predetermined range from the companion device the signal transmitted by the monitored person device may be very weak. This results in a very low power requirement for that feature on the monitored person device. In certain embodiments the monitored person device may broadcast two (2) or more distinct signals, of unique characteristics, for reception by the respective companion device. This arrangement provides for a more accurate determination of a spacing between the monitored person device and the respective companion device.

In any of the embodiments, the means to send a signal may be performed by various types of equipment, as conventionally known in the art, depending upon the type of signal being sent. Many of these methods may be employed with the present invention.

Referring now to FIG. 1, central location 22 transmits a signal utilizing coupling 58 to detached sending unit 24. Detached sending unit 24 transmits signal 56 to transportable device 26. A transmission antenna 160 of transportable device 26 broadcasts signal 114 for reception by receiving unit 30. Receiving unit 30 transfers signal 114 to central location 22 utilizing coupling 72. A transmission antenna 162 of monitored person device 28 transmits signal 110 for reception by transportable device 26.

Referring now to FIG. 3, detached sending units 34 transmit signals 60, 62 and 64 respectively for subsequent reception by companion device 38. A transmission antenna 164 of companion device 38 transmits signal 136 for reception by receiving unit 44. Receiving unit 44 transfers signal 136 utilizing coupling 72 to central location 22. Central location 22 transmits a signal utilizing coupling 74 to transmitting unit 36. Transmitting unit 36 transmits signal 134 to companion device 38. A short range transmission antenna 166 of companion device 38 transmits signal 122 to monitored person device 40. A short range transmission antenna 168 of monitored person device 40 transmits signal 126 to companion device 38. A very short range transmission antenna 170 of medical monitoring device 42 transmits signal 130 to monitored person device 40. Alternatively, signal 130 may to transferred utilizing a wired connection.

Referring now to FIG. 4, central location 22 transmits a signal utilizing coupling 70 to detached sending units 48. Detached sending units 48 transmits signals 66 and 68 respectively for reception by transportable device 50. A short range transmission antenna 172 of transportable device 50 transmits signal 146 for reception by monitored person device 52. A short range transmission antenna 174 of monitored person device 52 transmits signal 142 for reception by transportable device 50. A long range transmission antenna 176 of transportable device 50 transmits signal 148 for reception by receiving unit 54. Receiving unit 54 transfers signal 148 utilizing coupling 72 to central location 22.

Referring now to FIG. 6, a short range transmission antenna 178 of base station 78 transmits signal 154 to transportable device 152. A short range transmission antenna 180 of transportable device 152 transmits signal 158 to base station 78. Base station 78 transfers a signal to central location, not shown in this view, utilizing phone line 76.

While separate elements are depicted on respective devices in the various views for transmission of signals to different components of the various depicted systems, a single element may act to transmit plural signals to separate components if desired. Similarly, where a single element is depicted to transmit a signal, multiple elements may be employed.

Temporal Marking Means

In certain situations it is desired to provide for an indication of when certain select references were generated. This desire is a requirement when the reference is going to be stored for historic use. The term temporal, as used herein, carries the common or conventional definition meaning 'of or pertaining to time'. Therefore, the term temporal marking refers to marking, or providing a distinct reference, of when in time an event occurred, within at least a range of time references. It is possible to provide for a temporal marking, or time measurement marking, of each reference utilizing equipment on the companion device or on the monitored person device contemporaneously with receipt of the signal(s) upon which the reference is based. It is also possible to provide for creation of the temporal marking at the time of receipt at the central location. Alternatively, the temporal marking may be created at any desired point between receipt of the signal upon which the reference is based and receipt at the central location. Generally, it is preferred to have such temporal marking contemporaneously created with each reference. It is possible, and in certain situations preferred, to assign a range to a group of references. This method is particularly expedient when performing batch transfers from the companion device. In certain uses a single time range will have several references associated therewith. The term occurrence reference as used herein refers to the end result data created indicative, within at least a range, of when an event occurred.

Figure 5:
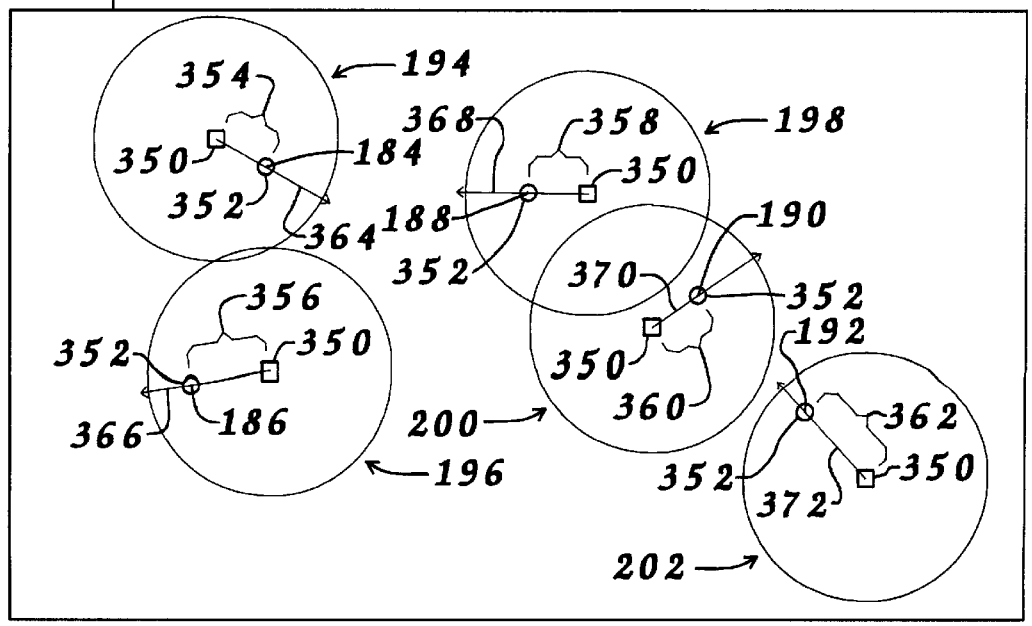
FIG. 5 is a plan view of a block with various locational references and associated occurrence references distributed therein.

FIG. 5 depicts, within a block 182, a series of five locational references 184, 186, 188, 190 and 192 each having an associated occurrence reference 194, 196, 198, 200 and 202 respectively. Each locational reference 184, 186,188,190 and 192 would have a set of coordinates, or other acceptable identifying reference, associated therewith. Each associated occurrence reference 194, 196, 198, 200 and 202 would have a set of identifying information which are, or may be converted to, date and time references. In this example each adjacent sequential associated occurrence reference 194, 196, 198, 200 and 202 are a uniform measurement of time apart.

Figure 7:
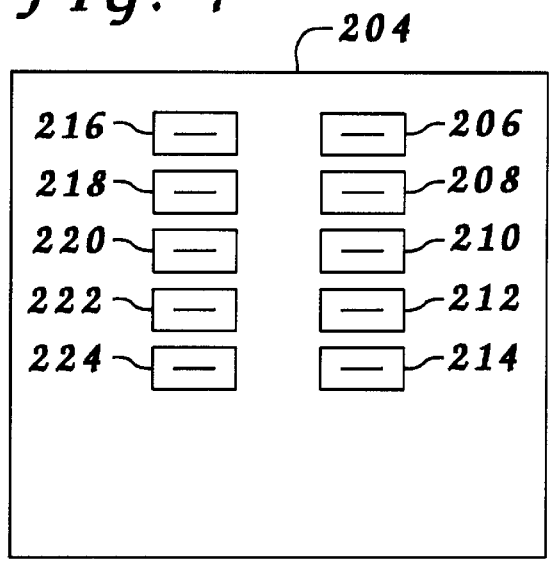
FIG. 7 is a plan view of a representation of a database with various bodily signal references and associated occurrence references therein.

FIG. 7 depicts, within a database 204, a series of five bodily signal references 206, 208, 210, 212 and 214 each having an associated occurrence reference 216, 218, 220, 222 and 224 respectively. Each bodily signal reference 206, 208, 210, 212 and 214 would have a data string containing information about a respective bodily function, associated therewith. Each associated occurrence reference 216, 218, 220, 222 and 224 would have a set of identifying information which are, or may be converted to, date and time references. In this example each adjacent sequential associated occurrence reference 216, 218, 220, 222 and 224 are a uniform measurement of time apart. Alternatively, each string of bodily function references may have a beginning occurrence reference and an ending occurrence reference. From these occurrence references and the number of uniformly spaced bodily function references it is possible to determine an occurrence reference for each respective bodily function reference.

Figure 10:
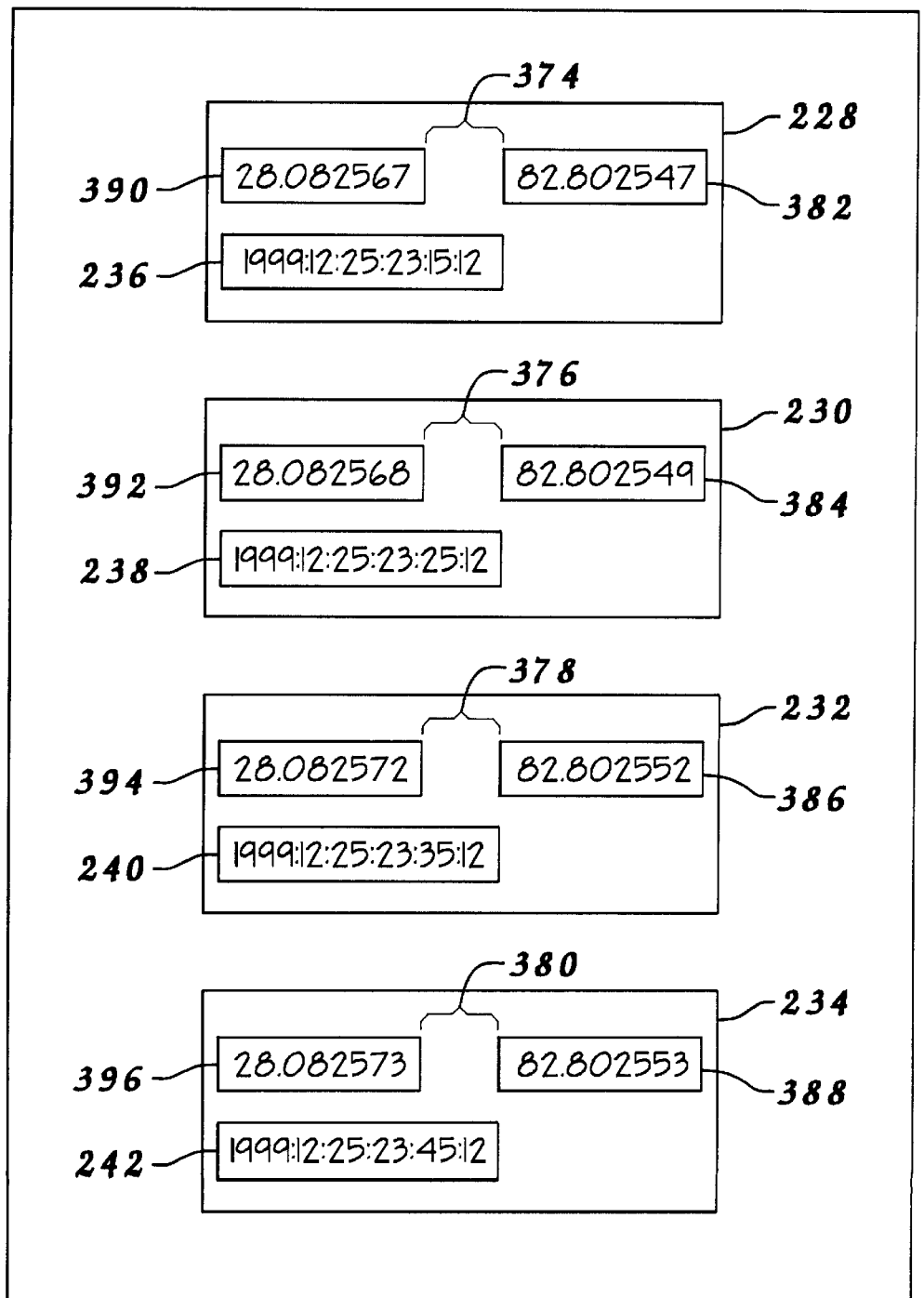
FIG. 10 is a plan view of a representation of a database.

FIG. 10 depicts, within a database 226, four (4) datasets 228, 230, 232 and 234. Each dataset 228, 230, 232 and 234 have an associated occurrence reference 236, 238, 240 and 242 respectively indicative of what time frame the associated dataset 228, 230, 232 or 234 relates.

Reference Storage Means

It is often a requirement that bodily signal references be stored, along with associated occurrence references indicative of what time span the respective references were associated with, in a database. It is often a requirement that locational references be stored, along with associated occurrence references indicative of what time span the respective references were associated with, in a database. Such storage provides for historic use of the data stored for various useful purposes. These references may be stored in separate databases or they may be stored in a common database, if both types of references are being created within the deployed system.

Numerous methods are known in the art for electronic storage of data which permit subsequent retrieval based upon select models. Many of these methods may be employed with the present invention. It being understood that such storage of bodily signal references, locational references and associated occurrence references are not required for all embodiments of the invention.

When required, each reference will be stored along with the associated occurrence reference. As mentioned, it is possible to assign a single range to a series of associated occurrence references. Alternatively, it is possible to provide for storage of select references taken from the totality of references available. One example uses a computer program which examines the series of references and identifies sequential strings of references within the series which do not vary beyond a predetermined tolerance range from all other references within the string. The computer program would then purge from the system all data between the first reference and the last reference within the string. This is particularly expedient where the monitored person is stationary for a long period of time, as example by sleeping for a number of hours in a generally stationary location or where the bodily function being monitored does not fluctuate widely.

FIG. 3 depicts a computer 244 having a storage device 246. Computer 244 is linked via coupling 72 to receiving unit 44 which receives signal 136 which contains data transmitted by companion device 38. At least select information contained in signal 136, following any conversion, if required, is stored within storage device 246 as a database 248. Database 248 may contain a sequence of data references 250. Data references 250 may be either locational references and/or bodily signal references. Database 248 may also contain a sequence of associated occurrence references 252 containing information about the time, or period of time, associated with each respective data reference 250.

Figure 13:
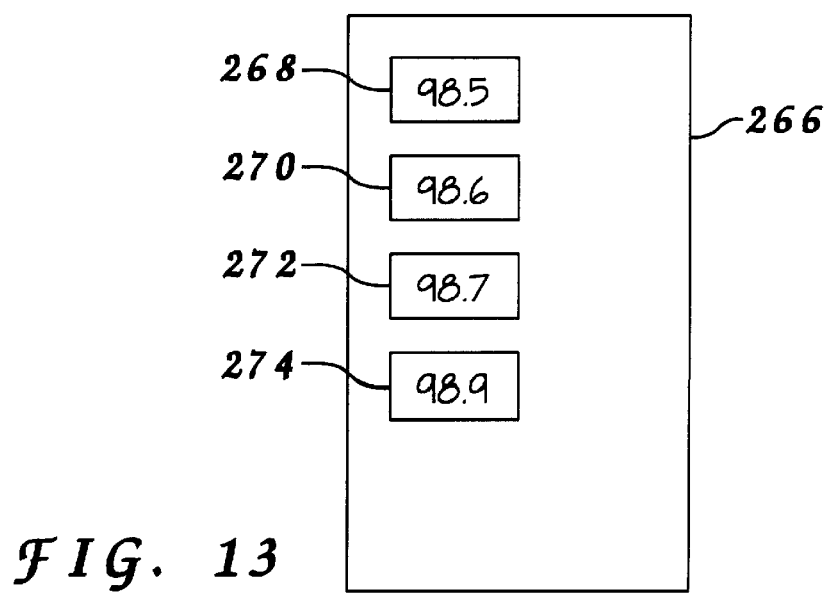
FIG. 13 is a plan view of a representation of a bodily signal conditional database.
Figure 15:
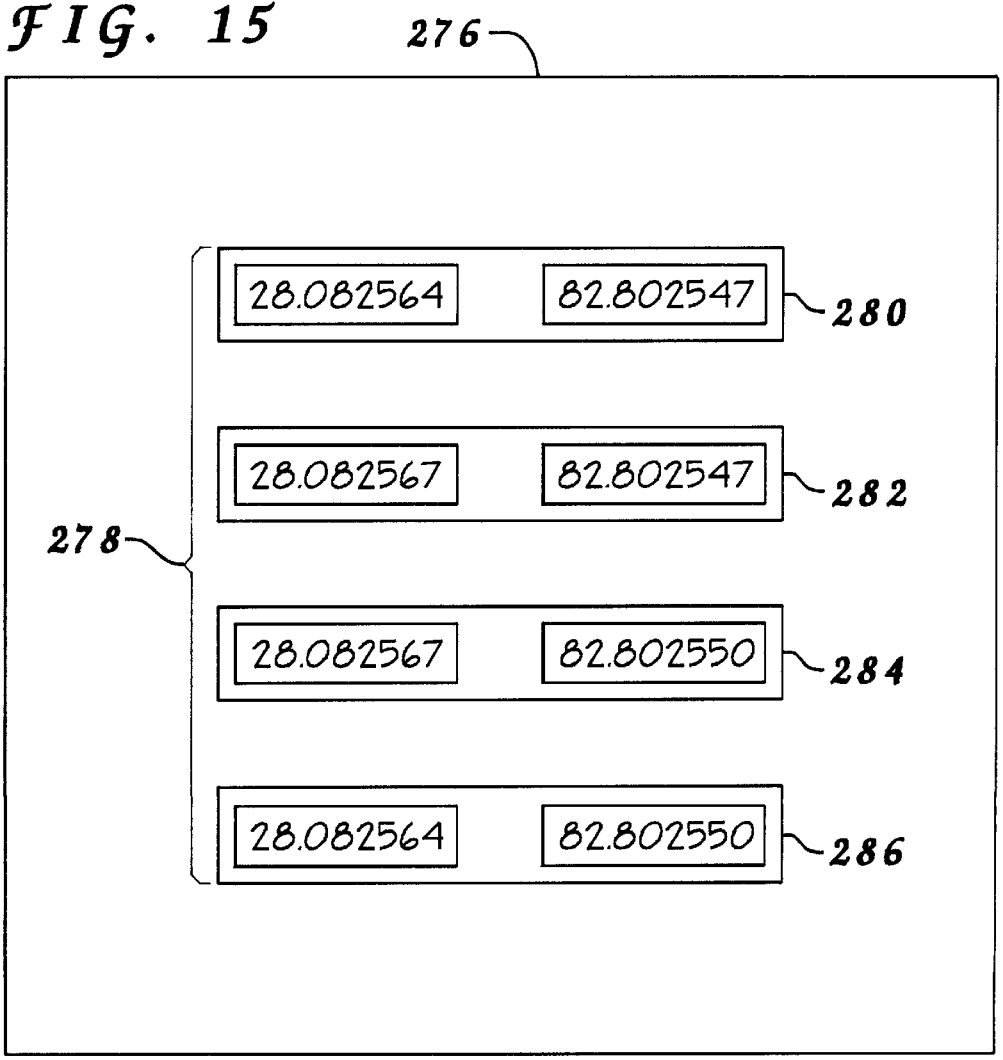
FIG. 15 is a plan view of a representation of a site defining database.

FIG. 9a through FIG. 9f depict databases 254, 256, 258, 260, 262 and 264 respectively which contain various information about specific bodily functions. FIG. 10 depicts datasets 228, 230, 232 and 234 which contain various information about specific locations including information indicative of a time of occurrence. FIG. 13 depicts a database 266 containing four (4) references 268, 270, 272 and 274. FIG. 15 depicts a site defining database 276 having a site set 278 having locational references 280, 282, 284 and 286. Each locational reference 280, 282, 284 and 286 define a corner of a physical site which may be an allowable site or an excluded site for the respective monitored person. alternatively, site defining database 276 may be created subsequent to storage of locational references for historic comparison.

Monitoring Means

A monitoring of a person under the present invention may include a determination of measurements of select bodily functions of the person. Examples of such bodily functions include blood pressure, (systolic and diastolic), heart beat rate, respiration rate, bodily temperature, blood oxygen level and blood alcohol level, amongst others. Devices are conventionally known in the art which may measure such functions in a non invasive manner (without requiring mechanical penetration of the body of the monitored person). These devices are exampled by passive contact of a portion of the device with the skin of the person or by manipulation of a portion of the device by the person, as exampled by a tubular member into which the person breathes. When passive contact is utilized the contact may be with a sensor positioned on the monitored person device or may be with a patch attached to the skin of the monitored person. When the patch is utilized, contact with the monitored person device may be direct, as exampled by a lead therebetween, or may be indirect, as exampled by a wireless broadcast. Such patches are known in the art capable of monitoring bodily functions or which measure for the presence of select drugs in the system of the monitored person. Many different medical test equipment exists in the art to perform various test to determine a respective specific status of a patient. Numerous of these medical test equipment may be utilized within a system under the present invention. These include select members of those medical test equipment which rely upon manipulation of a composition (such as a chemical or a drug) during the test process.

A particularly expedient concealment method for a monitoring device which utilizes passive contact involves concealment in an article typically worn in a surrounding engagement by a person. Examples of such articles include a bracelet or a watch which is worn about a wrist, an anklet which is worn about an ankle, a ring which is worn about a finger or a tightly worn necklace which is worn about a neck. When combined with a wireless transfer to the monitored person device this method provides many benefits over the patch type monitoring device. When the monitoring device is concealed as a watch, it is possible to provide for the device to perform the functions conventionally performed by watches. Another advantage of concealment in an article typically worn by a person involves the conventionally known method of measuring blood oxygen level utilizing a reflective light emitting diode monitoring device.

While it is preferred to utilize sensors which may make their readings based on no more than passive contact with the monitored person, it is possible to provide for implantation of a sensor under the skin of, or otherwise within, the monitored person. When utilizing either implanted sensors or contact sensors, it is possible for the sensor to transfer, preferably by wireless transfer, a signal to the monitored person device in possession of the monitored person. Alternatively, the sensor may be a part of the monitored person device.

It is possible to provide for a monitoring of multiple bodily functions. One example involves a first bodily function which is constantly, or at least frequently, monitored. If this bodily function deviates from a predefined range, then the second bodily function begins to be monitored.

FIG. 3 depicts medical monitoring device 42 capable of monitoring at least one bodily function of a monitored person, not shown in this view. medical monitoring device 42 transfers information about the bodily function utilizing signal 130 to monitored person device 40 for subsequent transfer to companion device 38 and eventual transfer to central location 22.

FIG. 8a and FIG. 8b depict monitored person device 102 having a skin contact surface 288 which would be held in contact with the skin of the monitored person, not shown in these views, during deployment. This deployment may be on any portion of the body of the monitored person required to provide for adequate testing of the bodily function(s) being monitored. Skin contact surface 288 has a series of contacts 290 which, when held in contact with human skin, may provide input to provide for a measurement of various body functions of the person. These contacts 290 may read, and/or produce various signals including electrical impulses and/or pressure changes and/or light reflective properties. This provides for other connected equipment within, or about, monitored person device 102 to make determinations, based on input from contacts 290, of select bodily functions including blood pressure, heart beat rate, respiration rate, bodily temperature and blood oxygen level. A breath tube 292 is depicted in a stored position 294, see FIG. 8a, and in a deployed position 296, see FIG. 8b. Breath tube 292 may be deployed when required and the monitored person may be required to blow therein to allow for measurement of blood alcohol level.

Bodily Signal Reference Creation Means

It is conventionally known in the art to convert measurements of each applicable bodily function to a data reference. These data references, or bodily signals, generally match conventional measurement methods or at least allow ready conversion to conventional measurement methods. One example of such a conventional measurement method is conversion of the respective bodily function cycle to a number of repetitions in a defined period of time, such as one (1) minute. Other examples include measurement of a pressure, or a lower and upper pressure range. Any conventional method may be utilized to reduce the measurement taken to a data reference.

FIG. 9a depicts database 254 comprised of a series of three (3) bodily signal references 298, 300 and 302 containing data indicative of blood pressure readings for a monitored person, not shown.

FIG. 9b depicts database 256 comprised of a series of three (3) bodily signal references 304, 306 and 308 containing data indicative of heart beat rate readings for a monitored person, not shown.

FIG. 9c depicts database 258 comprised of a series of three (3) bodily signal references 310, 312 and 314 containing data indicative of respiration rate readings for a monitored person, not shown.

FIG. 9d depicts database 260 comprised of a series of three (3) bodily signal references 316, 318 and 320 containing data indicative of bodily temperature readings for a monitored person, not shown.

FIG. 9e depicts database 262 comprised of a series of three (3) bodily signal references 322, 324 and 326 containing data indicative of blood oxygen readings for a monitored person, not shown.

FIG. 9f depicts database 264 comprised of a series of three (3) bodily signal references 328, 330 and 332 containing data indicative of blood alcohol readings for a monitored person, not shown.

Any of the conversion methods conventionally known in the art may be utilized to convert applicable sensor data into respective database 254, 256, 258, 260, 262 or 264.

Locational Determining Means

Various systems, and devices based upon those systems, exist to provide for a determination of a locational position. Several of these system are capable of making such a determination within a fairly narrow range of measurement. One group of such systems rely upon transmissions from satellites in orbit around our planet. Another group relies upon transmissions from ground based transmitters. Another group relies upon transmissions from a combination of satellites and ground based transmitters. Several of these systems, as exampled by differential global positioning systems, include the ability to identify an elevational height, or altitude, as well as a locational position. Such determination may be extremely desirable where the locational position is within a building having multiple floors such as a skyscraper.

The present invention requires that a series of calculations be performed to eventually arrive at a locational reference indicative of a specific location, within an acceptable range, of the monitored person device. These calculations will utilize at least the signal(s) received by the companion device from the detached sending unit(s) and the signal received by the companion device from the monitored person device.

Without regard for the transmission system employed to generate a signal, or signals, each companion device will routinely receive at least two (2) signals. The first signal(s) being from the detached sending unit(s) and the second signal from the monitored person device. These signals are then capable of, through a mathematical computation, being reduced to a locational reference indicative of a specific location, within a predetermined range of measurement, of the monitored person device.

It is possible that the mathematical computation will be performed within the companion device. Alternatively, raw data may be sent within the signal of the transmitting means of the companion device with the mathematical computation occurring subsequent to receipt of the signal by the transmission acquisition means, as exampled by at the central location.

It is possible, and preferred in certain deployments, to have a reliance upon a primary transmission system and at least one backup transmission system. The signal(s) from the primary transmission system may be indefinite or totally absent, in which case the mathematical computation based on the signal(s), if any, received by the companion device from the primary transmission system would be incapable of eventually determining a locational reference of the monitored person device. In that case the companion device would switch through any backup transmission systems until the received signal(s) was present and of a quality suitable for use to eventually arrive at a locational reference for the monitored person device.

One example which follows makes use of Global Positioning Satellites (G.P.S.), as conventionally known in the art, for determining a locational position of the respective monitored person device. This method of determining locational position is particularly desirable due to the wide coverage area and the accuracy afford by such usage. Numerous other methods, all conventionally known in the art, are adaptable for usage with the present invention. Another example make use of ground based transmitters, also conventionally known in the art.

It is a requirement that it be possible to determine, within at least a select range, both the spacing (distance) between and the orientation (direction) of the monitored person device relative to the respective companion device. This will allow for a locational reference to be created for the monitored person device following a determination of the location of the respective companion device. Numerous methods, and systems based upon those methods, exist to determine the spacing between and or the relative orientation of, a first device and a second device. Many of these methods may be employed for the present invention.

FIG. 1 depicts system 20 capable of relatively accurately determining, or otherwise creating, a locational reference 334 indicative of locational position 84 of monitored person device 28. This determination is performed by determining locational position 80 of transportable device 26 then determining relative position 82 involving spacing and orientation of monitored person device 28 from transportable device 26.

FIG. 3 depicts system 32 similarly capable of determining a locational reference 336 of monitored person device 40 following performing mathematical computations including those indicative of a locational reference 338 of companion device 38. Companion device 38 receives signal 60, signal 62 and signal 64 from detached sending units 34 and signal 126 from monitored person device 40. Companion device 38 may then transfer such signals, along with any distinct signal(s) created within companion device 38 which may be required to computate locational reference 336 of monitored person device 40, to central location 22. Alternatively, companion device 38 may perform the required mathematical computations and transfer the actual locational reference 336. While companion device 38 is depicted as having features to provide for reception of signals 60, 62 and 64 from which locational reference 338 may be determined, alternatively locational reference 338 may be transferred once to system 32 from a detached sending unit. This is particularly expedient when companion device 38 is to remain stationarily positioned following installation.

FIG. 4 depicts system 46 including transportable device 50 and monitored person device 52. Transportable device 50 contains structures which enable a determination of a locational reference 340 indicative of its locational position. Transportable device 50 further contains a first locational device 342 while monitored person device 52 contains a second locational device 344. First locational device 342 and second locational device 344 provide for a determination of a general directional indication and a general spacing indication wherein a locational position 346 of monitored person device 52 may be made relative to locational reference 340 of transportable device 50. In such a manner it is possible to make a determination, utilizing methods conventionally known in the art, of a locational reference 348 (within a reasonable variation) of monitored person device 52 without requiring more complicated equipment located on monitored person device 52.

FIG. 5 depicts relative orientations of a transportable device 350 and a monitored person device 352 as viewed collectively at five (5) distinct time frames represented by five (5) occurrence references 194, 196, 198, 200 and 202. A system, not shown in this view, would acquire information sufficient to allow for a fairly accurate determination of a respective locational reference 184, 186, 188, 190 and 192 of transportable device 350. The system would also acquire information sufficient to allow for a fairly accurate determination of a respective spacing 354, 356, 358, 360 and 362 of monitored person device 352 from transportable device 350. The system would also acquire information sufficient to all for a fairly accurate determination of a respective orientation 364, 366, 368, 370 and 372 of monitored person device 352 from transportable device 350. Utilizing at least this information the system would then be capable of fairly accurately determining locational reference 184, 186, 188, 190 and 192 of monitored person device 352.

Locational Reference Creation Means

Numerous reference methods, as conventionally known in the art, may be employed to define each locational reference, as exampled by a set of coordinates. One example of these coordinate references is those based upon a set of latitude, in degrees to a desired degree of precision, and longitude, in degrees to a desired degree of precision, references. Another example of these coordinate references include those based upon a set of distance, in any conventional measurement distance, and angular orientation, as exampled by degrees, references from a fixed locational reference.

FIG. 10 depicts database 226 having a series of datasets 228, 230, 232 and 234. Each dataset 228, 230, 232 and 234 has a locational reference 374, 376, 378 and 380 which respectively comprises a longitudinal reference 382, 384, 386 and 388 and a latitude reference 390, 392, 394 and 396. Each locational reference 374, 376, 378 and 380 identifies a specific locational position. Each dataset 228, 230, 232 and 234 further has associated occurrence reference 236, 238, 240 and 242 respectively which identifies approximately when in time the dataset relates to. Various methods may be utilized to create the various datasets 228, 230, 232 and 234. Various methods may be utilized to identify the various information associated with datasets 228, 230, 232 and 234.

Bodily Signal Conditional Database

In certain system configurations, it may be a desire to store various bodily signal conditional references created for each applicable respective monitored person being monitored. These conditional references would include a set of references, either inclusive or exclusive, which would provide for a comparison to determine if the respective monitored person was outside of an acceptable range for the particular bodily signal, or signals, being monitored. Such a database could be used to identify potentially dangerous medical conditions.

The bodily signal conditional database could be identical for all monitored persons, could be specific to the monitored person or could be based on specific characteristics of the monitored person as exampled by age, weight, sex, other factors or any desired combination thereof. The bodily signal conditional database preferably is stored within, or about, either the companion device or the monitored person device but may be stored at the central location.

Figure 11:
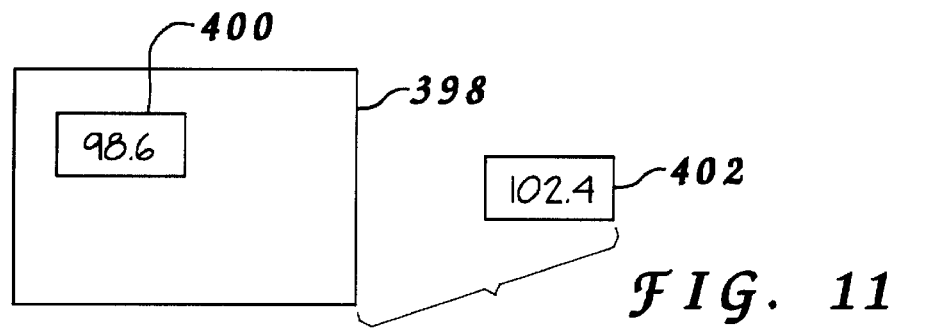
FIG. 11 is a plan view of a representation of a bodily signal conditional database and a plan representation of a comparative bodily signal reference.

FIG. 11 depicts a bodily signal conditional database 398 having a baseline measurement 400 for a specific bodily function. A comparative bodily signal reference 402 may be compared to baseline measurement 400 utilizing a mathematical computation which would establish an acceptable range to determine if the comparative bodily signal reference 402 is within the range, or acceptable, or outside of the range, or unacceptable.

Figure 12:
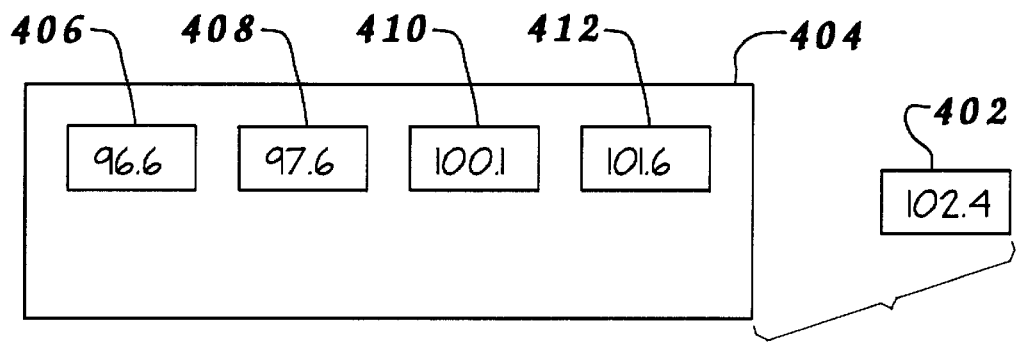
FIG. 12 is a plan view of a representation of a more sophisticated bodily signal conditional database and a representation of a comparative bodily signal reference.

Alternatively, multiple comparative references specific to the bodily function being monitored may exist, as exampled by a bodily signal conditional database 404 as depicted in FIG. 12. In this example, a dangerous lower threshold 406, a warning lower threshold 408, a warning upper threshold 410 and a dangerous upper threshold 412 may be defined within bodily signal conditional database 404. If comparative bodily signal reference 402 reaches, or passes, either warning lower threshold 408 or warning upper threshold 410 a first signal would be produced for subsequent action by the overall system or a portion thereof. If comparative bodily signal reference 402 subsequently reaches, or passes, either dangerous lower threshold 406 or dangerous upper threshold 412 a second signal would be produced for subsequent action by the overall system or a portion thereof.

Locational Conditional Database

In certain system configurations, it may be a desire to store various locational conditional references created for each applicable respective monitored person being monitored. These conditional references would include a set of references, either inclusive or exclusive, which would provide for a comparison to determine if the respective monitored person was either inside or outside of an allowable roaming area or outside or inside of an excluded roaming area, or areas, for the respective monitored person.

Figure 14:
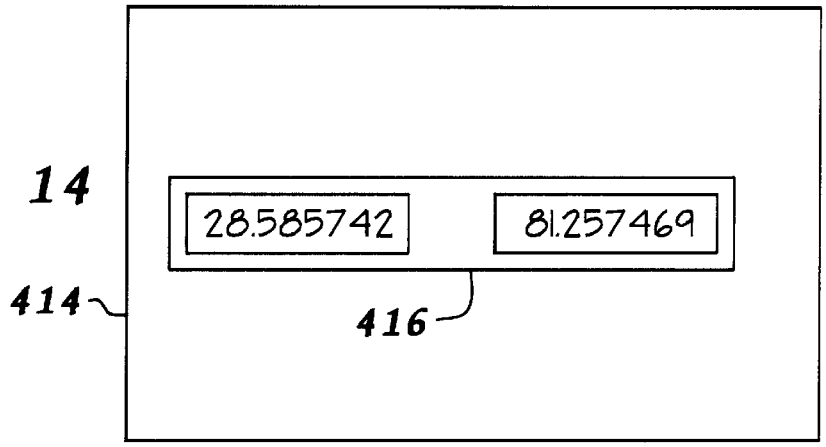
FIG. 14 is a plan view of a representation of a positional conditional database.

FIG. 14 depicts a locational conditional database 414 having a reference 416. A specific locational reference, disclosed elsewhere herein, may be compared to reference 416 utilizing a mathematical computation which would establish if the comparative locational reference was acceptable or unacceptable in comparison to reference 416. The mathematical computation may define complex perimeters relative to reference 416 or may define a radial perimeter thereabout.

FIG. 15 depicts site defining database 276 having site set 278 having a series of locational references 280, 282, 284 and 286. Site defining database 276 is an example of a locational conditional database. In this example site set 278 defines a generally rectangular shaped site while many different shapes are possible. Site defining database 276 may have any number of such site sets 278. The site sets 278 which make up site defining database 276 may define included locations where presence is allowed, excluded locations where presence is not allowed or a combination thereof. Site defining database 276 may have any desired number of such series as required to adequately define included locations, excluded locations or a combination thereof. A specific locational reference, disclosed elsewhere herein, may be compared to any site sets 278 utilizing a mathematical computation which would establish if the comparative locational reference was acceptable or unacceptable in comparison to the series of references.

FIG. 16a and FIG. 16b depict a locational reference 418 and a locational reference 420 respectively. Locational reference 418 is received by central location 22 subsequent to transmission by companion device, not shown in these views. An excluded site 422 is defined by four (4) locational references 280, 282, 284 and 286 of site defining database 276, see FIG. 15, which are positioned at each corner thereof, not drawn to scale. It being understood that a computer program, as programable using methods conventionally known in the art, may be created which is capable of defining a boundary 424 based on locational references 280, 282, 284 and 286. Similarly, such a program could define any conceivable outline of a specific boundary. Boundary 424 extends around excluded site 422. The program could also be programed to determine if any specific locational reference is inside of boundary 424. FIG. 16a depicts locational reference 418 outside of excluded site 422. In this instance the program would not indicate, or otherwise report, a violation of excluded site 422. FIG. 16b depicts locational reference 420 positioned within excluded site 422. In this instance the program would indicate, and report, a violation of excluded site 422 by the applicable monitored person device, not shown in these views.

Comparison Means

There exist two modes of operation for comparison of references, either bodily signal or locational, of each monitored person. The first mode is real time comparison and the second is historic comparison. The real time comparison involves comparison of the bodily signal reference or the locational reference with the applicable respective bodily signal conditional database or locational conditional database contemporaneous with creation. (The term real time comparison is not meant to convey simultaneous comparison, but rather may have the actual comparison occurring at a slightly later time.) The historic comparison involves comparison of the applicable reference, either bodily function or locational, to a later defined set of comparative data. The real time comparison may be made directly within the companion device or monitored person device by having the respective conditional database contained therein respectively. Alternatively, the comparison of either type may be made at the central location by having the respective conditional database stored thereat.

a. Immediate Comparison

Comparison of the bodily signal references against the bodily signal conditional database for a respective monitored person may occur immediately subsequent to creation thereof, within the companion device or within the monitored person device, or when received by the central location. Comparison of the locational references against the locational conditional database for a respective monitored person may occur immediately subsequent to creation thereof, within the companion device or within the monitored person device, or when received by the central location.

FIG. 16a and FIG. 16b depict an immediate comparison of contemporaneously created locational reference 418 and locational reference 420 with an established excluded site 422. Locational reference 418 and locational reference 420 are respectively received by central location 22 subsequent to transmission by the companion device, not shown in these views. Excluded site 422 has previously been defined by four (4) locational references 280, 282, 284 and 286 which are positioned at each corner thereof. It being understood that a computer program, as programable using methods conventionally known in the art, may be created which is capable of defining boundary 424 based on locational references 280, 282, 284 and 286. Similarly, such a program could define any conceivable outline of a specific boundary. Boundary 424 extends around excluded site 422. The program would also be programed to determine if any specific locational reference is inside of boundary 424. FIG. 16a depicts locational reference 418 outside of excluded site 422. In this instance the program would not indicate, or otherwise report, a violation of excluded site 422. FIG. 16b depicts locational reference 420 positioned within excluded site 422. In this instance the program would indicate, and report, a violation of excluded site 422.

FIG. 11 depicts comparative bodily signal reference 402 which is compared contemporaneously to baseline measurement 400 of bodily signal conditional database 398 in real time. Variation of comparative bodily signal reference 402 beyond a predetermined range from baseline measurement 400 results in a predetermined activation of a response by the system.

b. Historic Comparison

It is possible to historically utilize recorded locational references and/or bodily signal references for several useful purposes including for law enforcement investigation and medical evaluation of the monitored person.

FIG. 17 depicts a street 426 and a street 428 intersecting one another. A vacant lot 430 is situated on one corner of street 426 and street 428. A comparative location reference 432 has been identified and is surrounded by a boundary 434. A comparative temporal reference, not shown, which has a range of temporal references, has been entered. In this example boundary 434 falls completely within vacant lot 430. A computer program, not shown, has examined all records within database 226, see FIG. 10, and has identified dataset 228, dataset 230, dataset 232 and dataset 234 which respectively have locational references 374, 376, 378 and 380 and occurrence references 236, 238, 240 and 242, which fall within the comparative temporal reference. Each dataset 228, 230, 232 and 234 were created as a result of a single monitored person device, not shown. Therefore, it is possible to determine which monitored person, if any, were within the later created comparative location reference 432 during a period of time represented by the comparative temporal reference.

FIG. 13 depicts database 266 having stored therein a series of references 268, 270, 272 and 274 associated with a bodily signal. These references may be historically examined to determine the status of the monitored person.

Monitored Person Notification Means

It is desirable to provide for notification of the monitored person indicative of various specific status of at least portions of the respective system. One example of this involves notifying the monitored person of the status of communication between the monitored person device and the companion device at least to warn when a limit of communication range is being approached. Other examples include notification of overall system status, notification of any responsive action being implemented by the system or personnel controlling the system and notification a status of that responsive action including estimated time of implementation of a specific action. Numerous devices are known in the art, and have associated methods, for providing people with messages. These devices include pagers and cell phones. Many of these methods may be employed with the present invention.

The actual activation of the specific notification may be initiated by several components of the respective system. These components include the monitored person device, the companion device, the central location or, when deployed, the medical monitoring device.

FIG. 4 depicts monitored person device 52 having an audio output 436 and an LED readout 438. Audio output 436 may give audio notification including specific sounds, programmed verbal announcements or verbal communication from live personnel. Audio output 436 may provide for two way communication between the monitored person and personnel at central location 22. LED readout 438 may give visual notification including text readout.

The various features disclosed herein primarily have been explained in the context of dual deployed component systems comprising a monitored person device and a companion device for each monitored person. It is envisioned that many of these features may be used in systems having a single deployed component for each monitored person which is retained by the respective monitored person. Such systems would provide for each respective single deployed component to have sufficient structures thereon to provide for at least the positional determining means. Such systems therefore would not require that a companion device be deployed with each respective single deployed component for the system to function.

With respect to the above description then, it is to be realized that the optimum dimensional relationships for the parts of the invention, to include variations in size, material, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A system to provide for identifying a locational reference for a monitored person, the system comprising:
   a) a monitored person device to be moved about with the monitored person during movement of the monitored person, the monitored person device comprising transmitting means to provide for generating a signal;
   b) a companion device about which the monitored person may freely move wherein the monitored person remains within a predefined spacing about the companion device, the companion device comprising:
      1) receiving means to provide for reception of the signal produced by the transmitting means of the monitored person device;
      2) transmitting means to provide for sending a signal to a detached receiving unit;
   c) locational determining means to provide for producing information from which a locational reference may be created indicative of a locational position of the companion device;
   d) computational means to provide for determining a locational position of the monitored person device utilizing at least:
      1) the information of the locational determining means indicative of the locational position of the companion device;
      2) the signal from the monitored person device received by the receiving means of the companion device;
      wherein the locational position of the companion device may be determined then a locational position of the monitored person device is determined based upon a determining of a spacing and an orientation of the monitored person device relative to the companion device, and;
   e) conversion means to provide for converting the locational position of the monitored person device to the locational reference for the monitored person.

2. The system defined in claim 1 wherein the system further comprises a plurality of monitored persons, a plurality of monitored person devices and a plurality of companion devices wherein each respective monitored person has a respective monitored person device and a respective companion device.

3. The system defined in claim 1 wherein the monitored person device further comprises:
   a) securing means to provide for a secure attachment of the monitored person device to the monitored person;
   b) tamper detection means to provide for detecting a tampering with the monitored person device attached to the monitored person.

4. The system defined in claim 1 wherein the monitored person device further comprises:
   a) receiving means to provide for reception of at least a portion of the signal from the transmitting means of the companion device;
   b) monitored person notification means to provide for notification of the monitored person of a message indicative of a status of the spacing between the companion device and the monitored person device.

5. The system defined in claim 1 further comprising storage means to provide for an archival retention within a locational tracking database of a series of locational references.

6. The system defined in claim 5 further comprising temporal marking means to provide for indicating, within at least a range of temporal references, an associated occurrence reference indicative of when each of the locational references occurred, each of the temporal references stored within the locational tracking database.

7. The system defined in claim 1 wherein the locational determining means further provides for a detached sending unit to transmit a signal and wherein the receiving means of the companion device further provides for reception of the signal transmitted by the detached sending unit and wherein the detached sending unit is a ground based transmitter and wherein the computational means further utilizes the signal transmitted by the detached sending unit in determining the locational position of the companion device.

8. The system defined in claim 1 wherein the locational determining means further provides for a detached sending unit to transmit a signal and wherein the receiving means of the companion device further provides for reception of the signal transmitted by the detached sending unit and wherein the detached sending unit is an orbital based transmitter and wherein the computational means further utilizes the signal transmitted by the detached sending unit in determining the locational position of the companion device.

9. A system to provide for identifying a locational reference for a plurality of monitored persons, the system comprising:
   a) a plurality of companion devices, each respective companion device transportable to be manually moved about by a respective monitored person, each respective monitored person being one of the plurality of monitored persons, and wherein the respective monitored person retains the respective companion device within a predefined spacing about the respective monitored person, each companion device comprising:
1) first receiving means to provide for receiving signals from detached sending units;
2) second receiving means;
3) first transmitting means to provide for sending a signal to a detached receiving unit;
4) second transmitting means to provide for sending a signal;

b) a plurality of monitored person devices, each respective monitored person device to be moved about with the respective monitored person during movement of the respective monitored person, each monitored person device comprising:
1) receiving means to provide for receiving the signal from the second transmitting means of a respective companion device;
2) transmitting means to provide for generating a signal for reception by the second receiving means of the respective companion device;

c) computational means to provide for determining a locational position of the respective monitored person device utilizing at least:
1) the signals from the detached sending units received by the first receiving means of the respective companion device;
2) the signal from the respective monitored person device received by the second receiving means of the respective companion device;
wherein a locational position of the respective companion device is determined then a locational position of the respective monitored person device is determined based upon a determining of a spacing and an orientation of the respective monitored person device relative to the respective companion device, and;

d) conversion means to provide for converting the locational position of the respective monitored person device to the locational reference for the respective monitored person.

10. The system defined in claim 9 wherein each of the monitored person devices further comprises securing means to provide for a secure attachment of the respective monitored person device to the respective monitored person.

11. The system defined in claim 10 wherein each of the monitored person devices further comprises tamper detection means to provide for detecting a tampering with the respective monitored person device attached to the respective monitored person.

12. The system defined in claim 9 wherein each monitored person device further comprises monitored person notification means to provide for notification of the respective monitored person of a message indicative of a status of the spacing between the respective companion device and the respective monitored person device.

13. The system defined in claim 9 further comprising storage means to provide for an archival retention within a locational tracking database of a series of locational references for each of the respective monitored person devices.

14. A system to provide for monitoring a bodily function of a monitored person, and identifying a locational reference for the monitored person, the system comprising:
a) a companion device to be manually moved about by the monitored person wherein the monitored person retains the companion device within a predefined spacing about the monitored person, the companion device comprising:
1) first receiving means to provide for receiving signals from detached sending units;
2) second receiving means;
3) transmitting means to provide for sending a signal to a detached receiving unit;

b) a monitored person device to be moved about with the monitored person during movement of the monitored person, the monitored person device comprising:
1) monitoring means to provide for detecting a bodily signal produced by the monitored person;
2) transmitting means to provide for generating a signal for reception by the second receiving means of the companion device;

c) computational means to provide for determining a locational position of the monitored person device utilizing at least:
1) the signals from the detached sending units received by the first receiving means of the companion device;
2) the signal from the monitored person device received by the second receiving means of the companion device;
wherein a locational position of the companion device is determined then a locational position of the monitored person device is determined based upon a determining of a spacing and an orientation of the monitored person device relative to the companion device;

d) conversion means to provide for converting the locational position of the monitored person device to the locational reference for the monitored person, and;

e) bodily signal reference creation means to provide for creation of a bodily signal reference as detected by the monitoring means.

15. The system defined in claim 14 further comprises notification means to provide for making a notification to an oversight authority of the bodily signal reference and the locational reference of the monitored person in the advent of a medical emergency.

16. The system defined in claim 14 wherein the monitored person device further comprises:
a) receiving means to provide for a reception of at least a portion of the signal from the transmitting means of the companion device;
b) monitored person notification means to provide for a notification of the monitored person of a message indicative of a status of the spacing between the companion device and the monitored person device.

17. The system defined in claim 15 wherein the monitored person device further comprises:
a) receiving means to provide for reception of at least a portion of the signal from the transmitting means of the companion device;
b) monitored person notification means to provide for a notification of the monitored person of a message during the medical emergency indicative of:
1) the bodily signal reference;
2) a status of the notification made to the oversight authority.

18. The system defined in claim 14 further comprising storage means to provide for an archival retention within a locational tracking database of a series of locational references and a series of corresponding bodily signal references.

19. The system defined in claim 18 further comprising temporal marking means to provide for indicating, within at least a range of temporal references, an associated occurrence reference indicative of when each of the locational references and corresponding bodily signal references occurred, each of the temporal references stored within the locational tracking database.

20. The system defined in claim 14 wherein the system further comprises a plurality of monitored persons, a plurality of companion devices and a plurality of monitored person devices wherein each respective monitored person has a respective companion device and a respective monitored person device.

* * * * *